US007027143B1

(12) United States Patent
Stokowski et al.

(10) Patent No.: US 7,027,143 B1
(45) Date of Patent: Apr. 11, 2006

(54) METHODS AND SYSTEMS FOR INSPECTING RETICLES USING AERIAL IMAGING AT OFF-STEPPER WAVELENGTHS

(75) Inventors: Stan Stokowski, Danville, CA (US); David Alles, Los Altos, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 333 days.

(21) Appl. No.: 10/679,844

(22) Filed: Oct. 6, 2003

Related U.S. Application Data

(60) Provisional application No. 60/419,028, filed on Oct. 15, 2002.

(51) Int. Cl.
*G01N 21/00* (2006.01)
(52) U.S. Cl. .................. 356/237.2; 356/237.5
(58) Field of Classification Search ............... None
See application file for complete search history.

(56) References Cited

U.S. PATENT DOCUMENTS

| | | | |
|---|---|---|---|
| 4,247,203 A | 1/1981 | Levy et al. |
| 4,347,001 A | 8/1982 | Levy et al. |
| 4,378,159 A | 3/1983 | Galbraith |
| 4,448,532 A | 5/1984 | Joseph et al. |
| 4,532,650 A | 7/1985 | Wihl et al. |
| 4,555,798 A | 11/1985 | Broadbent, Jr. et al. |
| 4,579,455 A | 4/1986 | Levy et al. |
| 4,633,504 A | 12/1986 | Wihl |
| 4,641,967 A | 2/1987 | Pecen |
| 4,758,094 A | 7/1988 | Wihl |
| 4,766,324 A | 8/1988 | Saadat et al. |
| 4,805,123 A | 2/1989 | Specht et al. |
| 4,817,123 A | 3/1989 | Sones et al. |
| 4,845,558 A | 7/1989 | Tsai et al. |
| 4,877,326 A | 10/1989 | Chadwick et al. |
| 4,926,489 A | 5/1990 | Danielson et al. |
| 5,189,481 A | 2/1993 | Jann et al. |
| 5,453,844 A | 9/1995 | George et al. |

(Continued)

FOREIGN PATENT DOCUMENTS

EP        1 061 358        12/2000

(Continued)

OTHER PUBLICATIONS

Anton Barty, "Aerial Image Microscopes for the inspection of defects in EUV masks" 2002, 22 nd Annual BACUS Symposium on Photomask Technology, SPIE vol. 4889 (2002).*

(Continued)

*Primary Examiner*—Michael P. Stafira
(74) *Attorney, Agent, or Firm*—Ann Marie Mewherter; Daffer McDaniel, LLP

(57) ABSTRACT

Methods and systems for inspecting a reticle are provided. A method may include forming an aerial image of the reticle with an inspection system at a wavelength different from a wavelength of an exposure system. The method may also include correcting the aerial image for differences between modulation transfer functions (MTF) of the inspection system and the exposure system. In this manner, the corrected aerial image may be substantially equivalent to an image of the reticle that would be printed onto a specimen by the exposure system at the wavelength of the exposure system. In addition, the method may include detecting defects on the reticle using the corrected aerial image. The detected defects may include approximately all of the defects that would be printed onto a specimen by the exposure system using the reticle.

20 Claims, 11 Drawing Sheets

U.S. PATENT DOCUMENTS

| | | |
|---|---|---|
| 5,459,520 A | 10/1995 | Sasaki |
| 5,563,702 A | 10/1996 | Emery et al. |
| 5,572,598 A | 11/1996 | Wihl et al. |
| 5,608,538 A | 3/1997 | Edgar et al. |
| 5,619,548 A | 4/1997 | Koppel |
| 5,621,519 A | 4/1997 | Frost et al. |
| 5,689,614 A | 11/1997 | Gronet et al. |
| 5,737,072 A | 4/1998 | Emery et al. |
| 5,754,678 A | 5/1998 | Hawthorne et al. |
| 5,771,317 A | 6/1998 | Edgar |
| 5,774,179 A | 6/1998 | Chevrette et al. |
| 5,889,593 A | 3/1999 | Bareket |
| 5,980,187 A | 11/1999 | Verhovsky |
| 5,991,699 A | 11/1999 | Kulkarni et al. |
| 6,052,478 A | 4/2000 | Wihl et al. |
| 6,076,465 A | 6/2000 | Vacca et al. |
| 6,104,835 A | 8/2000 | Han |
| 6,122,017 A | 9/2000 | Taubman |
| 6,122,046 A | 9/2000 | Almogy |
| 6,137,570 A | 10/2000 | Chuang et al. |
| 6,141,038 A | 10/2000 | Young et al. |
| 6,175,645 B1 | 1/2001 | Elyasaf et al. |
| 6,184,929 B1 | 2/2001 | Noda et al. |
| 6,184,976 B1 * | 2/2001 | Park et al. ............... 356/237.4 |
| 6,233,719 B1 | 5/2001 | Hardikar et al. |
| 6,266,437 B1 | 7/2001 | Eichel et al. |
| 6,268,093 B1 * | 7/2001 | Kenan et al. ................. 430/30 |
| 6,282,309 B1 | 8/2001 | Emery |
| 6,344,640 B1 | 2/2002 | Rhoads |
| 6,363,166 B1 | 3/2002 | Wihl et al. |
| 6,466,315 B1 * | 10/2002 | Karpol et al. ............ 356/237.4 |
| 6,529,621 B1 | 3/2003 | Glasser et al. |
| 6,614,520 B1 | 9/2003 | Bareket et al. |
| 6,636,301 B1 | 10/2003 | Kvamme et al. |
| 6,691,052 B1 * | 2/2004 | Maurer ........................ 702/81 |
| 2001/0022858 A1 | 9/2001 | Komiya et al. |
| 2003/0207475 A1 * | 11/2003 | Nakasuji et al. .............. 438/14 |

FOREIGN PATENT DOCUMENTS

| | | |
|---|---|---|
| EP | 1 061 571 | 12/2000 |
| EP | 1 065 567 | 1/2001 |
| EP | 1 066 925 | 1/2001 |
| EP | 1 069 609 | 1/2001 |
| WO | 99/22310 | 5/1999 |
| WO | 99/25004 | 5/1999 |
| WO | 99/38002 | 7/1999 |
| WO | 99/41434 | 8/1999 |
| WO | 99/59200 | 11/1999 |
| WO | 00/03234 | 1/2000 |
| WO | 00/36525 | 6/2000 |
| WO | 00/68884 | 11/2000 |
| WO | 00/70332 | 11/2000 |
| WO | 01/09566 | 2/2001 |
| WO | 01/40145 | 6/2001 |

OTHER PUBLICATIONS

Pei-yang, "Printability of Pellicle Defects in DUV 0.5 um Lithography" 1991, SPIE vol. 1604 11 th Annual BACUS Symposium on Photomask Technology (1991).*

Otsu, "A Threshold Selection Method from Gray-Level Histograms," IEEE Transactions on Systems, Man, and Cybernetics, vol. SMC-9, No. 1, Jan. 1979, pp. 62-66.

* cited by examiner

| | Region | Location | Designation |
|---|---|---|---|
| Feature 74 | A1 | $(x,y)_{A1}$ | 0 |
| | A2 | $(x,y)_{A2}$ | 0 |
| | A3 | $(x,y)_{A3}$ | 1 |
| | A4 | $(x,y)_{A4}$ | 0 |
| | A5 | $(x,y)_{A5}$ | 0 |
| Feature 74 | A1 | $(x,y)_{A1}$ | 2 |
| | A2 | $(x,y)_{A2}$ | 3 |
| | A3 | $(x,y)_{A3}$ | 1 |
| | A4 | $(x,y)_{A4}$ | 3 |
| | A5 | $(x,y)_{A5}$ | 2 |
| Feature 74 | A1 | $(x,y)_{A1}$ | contact |
| | A2 | $(x,y)_{A2}$ | - |
| | A3 | $(x,y)_{A3}$ | gate |
| | A4 | $(x,y)_{A4}$ | - |
| | A5 | $(x,y)_{A5}$ | contact |

Fig. 5

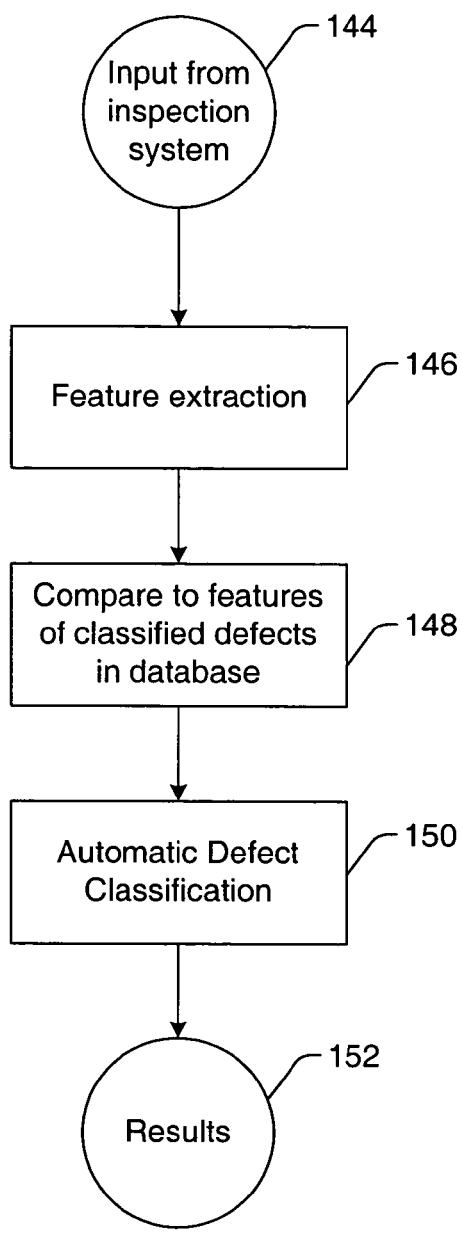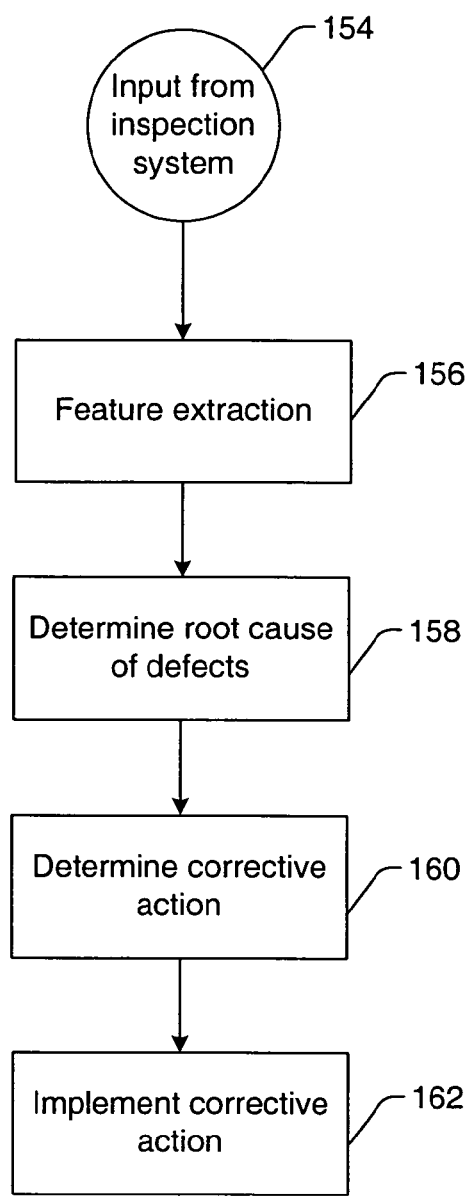
Fig. 10
Fig. 11

METHODS AND SYSTEMS FOR INSPECTING RETICLES USING AERIAL IMAGING AT OFF-STEPPER WAVELENGTHS

PRIORITY CLAIM

This application claims priority to U.S. Provisional Application No. 60/419,028 entitled "Methods and Systems for Inspecting Reticles Using Aerial Imaging at Off-Stepper Wavelengths," filed Oct. 15, 2002.

BACKGROUND OF THE INVENTION

1. Field of the Invention

This invention generally relates to systems and methods for reticle inspection. Certain embodiments relate to systems and methods for inspecting reticles using aerial imaging at off-stepper wavelengths.

2. Description of the Related Art

Semiconductor fabrication processes typically involve a number of lithography steps to form various features and multiple levels of a semiconductor device. Lithography involves transferring a pattern to a resist formed on a semiconductor substrate, which may be commonly referred to as a wafer. A reticle or a mask may be disposed above the resist and may have substantially transparent regions and substantially opaque regions configured in a pattern that may be transferred to the resist. As such, substantially opaque regions of the reticle may protect underlying regions of the resist from exposure to an energy source. The resist may, therefore, be patterned by selectively exposing regions of the resist to an energy source such as ultraviolet light, a beam of electrons, or an x-ray source. The patterned resist may then be used to mask underlying layers in subsequent semiconductor fabrication processes such as ion implantation and etch. Therefore, a resist may substantially inhibit an underlying layer such as a dielectric material or the semiconductor substrate from implantation of ions or removal by etch.

There are several types of reticles that are commercially available. For example, a reticle may be either a clear-field reticle or a dark-field reticle. A clear-field reticle has field or background areas that are opaque, and a dark-field reticle has field or background areas that are transparent. In addition, a binary reticle is a reticle having a patterned area that is either transparent or opaque. Binary reticles are different from phase-shift masks (PSM) that may include films that only partially transmit light, and these reticles may be commonly referred to as halftone or embedded reticles. If a phase-shifting material is placed on alternating clear spaces of a reticle, the reticle is referred to as an alternating PSM, an ALT PSM, or even a Levenson PSM. If a phase-shifting material is applied to arbitrary layout patterns, the reticle is referred to as an attenuated or halftone PSM, which may be fabricated by replacing the opaque material with a partially transmissive or "halftone" film. A ternary attenuated PSM is an attenuated PSM that includes OPC features. Each of the reticles described above may also include a pellicle, which is an optically transparent membrane that seals off the reticle surface from airborne particulates and other forms of contamination.

A process for manufacturing a reticle is similar to a wafer patterning process. For example, the goal of reticle manufacturing is forming a pattern in an opaque material such as a relatively thin chrome layer on a substantially transparent substrate such as glass. In addition, other appropriate opaque materials that may be used for reticle manufacturing include, but are not limited to, chromium, chromium oxide, and chromium nitride. Appropriate thicknesses for chrome layers may be approximately 1000 Å and may be deposited upon a glass substrate by sputtering. Additional appropriate transparent materials that may be used for reticle manufacturing include borosilicate glass or fused-silica ($SiO_2$, "quartz"), which have good dimensional stability and transmission properties for wavelengths of exposure systems. Additional materials may also be used for reticle manufacturing. For example, a film underlying an opaque material may act as an adhesion layer. Such an adhesion layer may include, for example, a mixture of chromium, nitrogen, and oxide. In addition, a film formed on top of the opaque material may act as an anti-reflective layer. An appropriate anti-reflective layer may be formed of, for example, a relatively thin layer of $Cr_2O_3$.

Reticle manufacturing may include a number of different steps such as pattern generation, which may include moving a glass substrate having a chrome layer and a resist layer formed thereon under a light source as shutters are moved and opened to allow precisely shaped patterns of light to shine onto the resist thereby creating the desired pattern. Since the patterns generated by an integrated circuit designer for each level are generally polygons, these patterns are decomposed into rectangles. The reticle pattern is transferred to the resist-covered reticle blank by a step-and-repeat process to create a master plate. The master plate is used to create multiple working reticle plates in a contact printer. The contact printer brings the master into contact with a resist-covered reticle blank and has an ultraviolet light source for transferring the image to the resist on the reticle blank.

Alternatively, reticles may be made with lasers or e-beam direct write exposure. Laser exposure allows the use of standard optical resists and is faster than e-beam direct write exposure. In addition, laser systems are also less expensive to purchase and operate. Direct write laser sources are turned on and off with an acousto-optical modulator (AOM). An example of a commercially available direct write laser system is the ALTA 3000® laser writer available from ETEC Systems, Inc., Hayward, Calif. Direct write e-beam systems are often used to manufacture complex reticles since they produce finer line resolution than laser systems. In addition, direct write e-beam systems can also write larger die sizes than laser systems. Examples of commercially available direct write e-beam systems include the MEBES 4500 and 5000 systems available from ETEC Systems, Inc.

After the exposure steps, the reticle is processed through development, inspection, etch, strip, and inspection steps to transfer the pattern into the opaque material. Defects in reticles are a source of yield reduction in integrated circuit manufacturing. Therefore, inspection of a reticle is a critical step in the reticle manufacturing process. As minimum pattern sizes shrink and integrated circuits are designed with higher device densities, defects that were once tolerable may no longer be acceptable. For example, a single defect may be repeated in each die in stepper systems and may kill every die in single-die reduction reticles. In addition, VLSI and ULSI-level integrated circuit manufacturing require substantially defect-free and dimensionally perfect reticles due to the critical dimension (CD) budget of such manufacturing. For example, the overall CD budget for such integrated circuits may be approximately 10% or better thereby resulting in a CD budget for a reticle with about a 4% error margin.

Defects may be a result of incorrect designing of the reticle pattern and/or flaws introduced into the patterns during the pattern generation process. Even if the design is correct, and the pattern generation process is performed satisfactorily, defects in the reticle may be generated by the reticle fabrication process as well as during subsequent processing and handling. In addition to the many potential causes of defects, there are also many different types of defects. For example, bubbles, scratches, pits, and fractures may be a result of a faulty raw glass substrate. Defects in the opaque material may include particulate inclusions in the material, pinholes or voids in the material surface, and invisible chemical anomalies such as nitrides or carbides that may lead to erratic local etching and undesired patterns. Defects such as voids in the resist layer may produce pinholes that may lead to chrome spots. In addition, localized characteristics in the resist may also produced variations in characteristics of the resist such as resist solubility across the reticle substrate. Particulate matter may also be introduced to the reticle during processing and/or handling of the reticle. Defects that may result in inoperative devices or which would cause a die to be rejected at final inspection are commonly referred to as "fatal" or "killer" defects, while other may be commonly referred to as "nonfatal" defects.

SUMMARY OF THE INVENTION

An embodiment of the present invention relates to a method for inspecting a reticle. The method may include forming an aerial image of the reticle using a set of exposure conditions. The set of exposure conditions may include exposure conditions within a process window of an exposure system. The reticle may include optical proximity correction (OPC) features. The OPC features may not be imaged in the aerial image. The method may also include detecting defects on the reticle by comparing the aerial image to a reference image. The reference image may be stored in a database. The reference image may be substantially optically equivalent to an image of the reticle that would be printed on a specimen by the exposure system under the set of exposure conditions. The reference image does not include images of the OPC features.

Therefore, a substantial portion of the defects may include defects that would be printed onto the specimen by the exposure system using the reticle under the set of exposure conditions.

A resist may be formed on the specimen. In one embodiment, the reference image may also be substantially optically equivalent to an image of the reticle generated from a pattern selected to be formed in a resist using the reticle. In this manner, the defects may be differences between the aerial image and an image that if printed onto a resist may produce a selected pattern in the resist. As such, the detected defects may include defects in a patterned resist that may be caused by the reticle.

In an embodiment, the method may include forming a plurality of aerial images of the reticle using different exposure conditions. Such a method may also include determining a process window of the exposure system using the plurality of aerial images.

In an additional embodiment, the method may include altering the aerial image to simulate performance characteristics of the exposure system and the specimen. In a further embodiment, the method may include detecting light reflected from the reticle and detecting defects on the reticle using the detected light.

In an embodiment, the reference image may include designations identifying different types of regions in the reference image. In this manner, different procedures may be used to detect defects in the different types of regions. In a further embodiment, the reference image may include designations identifying critical and non-critical regions of the reticle. In such an embodiment, the method may include indicating the defects that are detected in the critical regions. In yet another embodiment, the method may include determining if the reticle meets qualification criteria based on the detected defects.

An additional embodiment relates to another method for inspecting a reticle. The method may include forming an aerial image of the reticle. The reticle may include OPC features. The method may also include detecting defects on the reticle by comparing the aerial image to a reference image stored in a database. The reference image may not include images of the OPC features. The reference image may also include designations identifying different types of regions in the reference image. The method may also include any steps of other embodiments described herein.

A further embodiment relates to a system configured to inspect a reticle. The system may include an optical subsystem configured to form an aerial image of the reticle using a set of exposure conditions. The set of exposure conditions may include exposure conditions within a process window of the exposure system. The reticle may include OPC features. The OPC features may not be imaged in the aerial image. The system may also include a processor configured to detect defects on the reticle by comparing the aerial image to a reference image stored in a database. The reference image may be substantially optically equivalent to an image of the reticle that would be printed on a specimen by an exposure system under the set of exposure conditions. The reference image does not include images of the OPC features. As such, a substantial portion of the defects include defects that would be printed onto the specimen by the exposure system using the reticle under the set of exposure conditions.

A resist may be formed on the specimen. In one embodiment, the reference image may also be substantially optically equivalent to an image of the reticle generated from a pattern selected to be formed in a resist using the reticle. In this manner, the defects may be differences between the aerial image and an image that if printed onto a resist may produce a selected pattern in the resist. As such, the detected defects may include defects in a patterned resist that may be caused by the reticle.

In an embodiment, the optical subsystem may be configured to form a plurality of aerial images of the reticle using different exposure conditions. In such an embodiment, the processor may be configured to determine a process window of the exposure system using the plurality of aerial images. In an additional embodiment, the processor may be configured to alter the aerial image to simulate performance characteristics of the exposure system and the specimen. In a further embodiment, the optical subsystem may be configured to detect light reflected from the reticle. In such an embodiment, the processor may be configured to detect additional defects on the reticle using the detected light.

In an embodiment, the reference image may include designations identifying different types of regions on the reticle such that different procedures can be used by the processor to detect defects in the different types of regions. In an additional embodiment, the reference image may include designations identifying critical and non-critical regions of the reticle. In such an embodiment, the processor may be configured to indicate which of the defects are detected in the critical regions.

An additional embodiment relates to a system configured to inspect a reticle. The system may include an inspection subsystem configured to form a first aerial image of the reticle. The first aerial image may be used to detect defects on the reticle. The system may also include a review subsystem coupled to the inspection subsystem. The review subsystem may be configured to form a second aerial image of the reticle. The second aerial image may be used to analyze the defects. In an embodiment, the inspection and review subsystems may have common optics. In an alternative embodiment, the inspection and review subsystems may have separate optics and a common stage. In a further alternative embodiment, the inspection and review subsystems may have separate stages and a common handler. In an additional embodiment, the inspection and review subsystems may be coupled such that inspection and review may be performed substantially simultaneously.

Another embodiment relates to an additional system configured to inspect a reticle. The system may include an inspection subsystem configured to form a first aerial image of the reticle. The first aerial image may be used to detect defects on the reticle. The system may also include a review subsystem coupled to the inspection subsystem. The review subsystem may be configured to form a second aerial image of the reticle. The second aerial image may be used to analyze the defects. In addition, the system may include an image computer. The image computer may be configured to receive image data from the inspection and review subsystems representing the first and second aerial images.

The image computer may also be configured to perform one or more functions on the image data. For example, the one or more functions may include detecting defects on the reticle by comparing a first portion of the image data from the inspection subsystem to a second portion of the image data from the inspection subsystem. In an embodiment, the one or more functions may include detecting defects on the reticle by comparing image data from the inspection subsystem to a reference image of the reticle stored in a database. The image computer may be further configured to generate a database that includes a reference image of the reticle. In an additional embodiment, the one or more functions may include detecting defects on the reticle using the image data from the inspection subsystem and classifying defects using the image data from the inspection subsystem or the review subsystem. In a further embodiment, the one or more functions may include detecting defects on the reticle using the image data from the inspection subsystem and determining a root cause of the defects using the image data from the inspection subsystem or the review subsystem.

In an embodiment, the image computer may be configured to run automated process control algorithms. In an additional embodiment, the image computer may be coupled to one or more process tools. Such an embodiment of an image computer may also be configured to send information to and receive information from the one or more process tools. In a further embodiment, the image computer may be configured to access a fab database. Such an image computer may be configured to send information to and receive information from the fab database. In yet another embodiment, the image computer may be a parallel processing system. The system may be further configured as described herein.

Yet another embodiment relates to a method for inspecting a reticle. The method may include inspecting the reticle by forming a first aerial image of the reticle while the reticle is disposed in a system. The method may also include detecting defects on the reticle using the first aerial image. In addition, the method may include reviewing the defects by forming a second aerial image of the reticle while the reticle is disposed in the system. The method may further include analyzing the defects using the second aerial image. In an embodiment, inspecting the reticle and reviewing the defects may be performed substantially simultaneously. In an additional embodiment, inspecting the reticle and reviewing the defects may be performed while the reticle is disposed upon a common stage of the system. In a further embodiment, the method may include altering optics of the system between inspection and review. In an alternative embodiment, the method may include moving the reticle from a first stage to a second stage between inspection and review using one handler. The method may further include additional steps of other methods as described herein.

An additional embodiment relates to a method for inspecting a reticle that includes forming an aerial image of the reticle with an inspection system at a wavelength different from a wavelength of an exposure system. The method may also include correcting the aerial image for differences between modulation transfer functions of the inspection system and the exposure system such that the corrected aerial image may be substantially equivalent to an image of the reticle that would be printed onto a specimen by the exposure system at the wavelength of the exposure system. In addition, the method may include detecting defects on the reticle using the corrected aerial image. A substantial portion of the defects may include defects that would be printed onto the specimen by the exposure system using the reticle.

In an embodiment, the method may include altering a parameter of the inspection system in response to variations in a parameter of the exposure system. The method may also include altering the corrected aerial image to determine images of the reticle that would be printed onto the specimen by the exposure system at various levels of a parameter of the exposure system. In an additional embodiment, the method may include altering the corrected aerial image to determine images of the reticle that would be printed onto the specimen by the exposure system at various focus settings of the exposure system. In another embodiment, the method may include altering the corrected aerial image to determine images of the reticle that would be printed onto the specimen by the exposure system at various dose settings of the exposure system. In yet another embodiment, the method may include altering the corrected aerial image to determine variations across the image that would be printed onto the specimen by the exposure system due to variations of a parameter of the exposure system across the reticle.

In an embodiment, the method may include altering the corrected aerial image to determine images of the reticle that would be printed onto the specimen by a plurality of exposure systems of the same make and model as the exposure system. In an additional embodiment, the method may include altering the corrected aerial image to determine images of the reticle that would be printed onto the specimen by a plurality of exposure systems used in a common fabrication facility.

Another embodiment relates to an additional method for inspecting a reticle. The method may include forming an aerial image of the reticle with an inspection system at a wavelength different from a wavelength of an exposure system. The inspection system may have a modulation transfer function approximately equal to a modulation transfer function of the exposure system. The method may also include detecting defects on the reticle using the aerial image. In an embodiment, the method may further include altering a parameter of the inspection system in response to variations in a parameter of the exposure system.

A further embodiment relates to a system configured to inspect a reticle. The system may include an inspection system configured to form an aerial image of the reticle at a wavelength different from a wavelength of an exposure system. The system may also include a processor configured to correct the aerial image for differences between modulation transfer functions of the inspection system and the exposure system such that the corrected aerial image may be substantially equivalent to an image of the reticle that would be printed onto a specimen by the exposure system at the wavelength of the exposure system. The processor may also be configured to detect defects on the reticle using the corrected aerial image. A substantial portion of the defects may include defects that would be printed onto the specimen by the exposure system using the reticle.

In an embodiment, the processor may be further configured to alter a parameter of the inspection system in response to variations in a parameter of the exposure system. In an additional embodiment, the processor may be configured to alter the corrected aerial image to determine images of the reticle that would be printed onto the specimen by the exposure system at various levels of a parameter of the exposure system. In a further embodiment, the processor may be configured to alter the corrected aerial image to determine images of the reticle that would be printed onto the specimen by the exposure system at various focus settings of the exposure system. In another embodiment, the processor may be configured to alter the corrected aerial image to determine images of the reticle that would be printed onto the specimen by the exposure system at various dose settings of the exposure system. In yet another embodiment, the processor may be configured to alter the corrected aerial image to determine variations across the image that would be printed onto the specimen by the exposure system due to variations of a parameter of the exposure system across the reticle.

In an embodiment, the processor may be configured to alter the corrected aerial image to determine images of the reticle that would be printed onto the specimen by a plurality of exposure systems of the same make and model as the exposure system. In an additional embodiment, the processor may be configured to alter the corrected aerial image to determine images of the reticle that would be printed onto the specimen by a plurality of exposure systems used in a common fabrication facility.

BRIEF DESCRIPTION OF THE DRAWINGS

Further advantages of the present invention may become apparent to those skilled in the art with the benefit of the following detailed description of the preferred embodiments and upon reference to the accompanying drawings in which:

FIG. 5 depicts content of an embodiment of a database structure that may be used to represent a layout of a reticle;

FIGS. 9 and 10 depict flow charts illustrating various embodiments of a method for classifying defects detected on a reticle;

FIG. 11 depicts a flow chart illustrating an embodiment of a method for determining a root cause of defects on a reticle;

Figure 1:
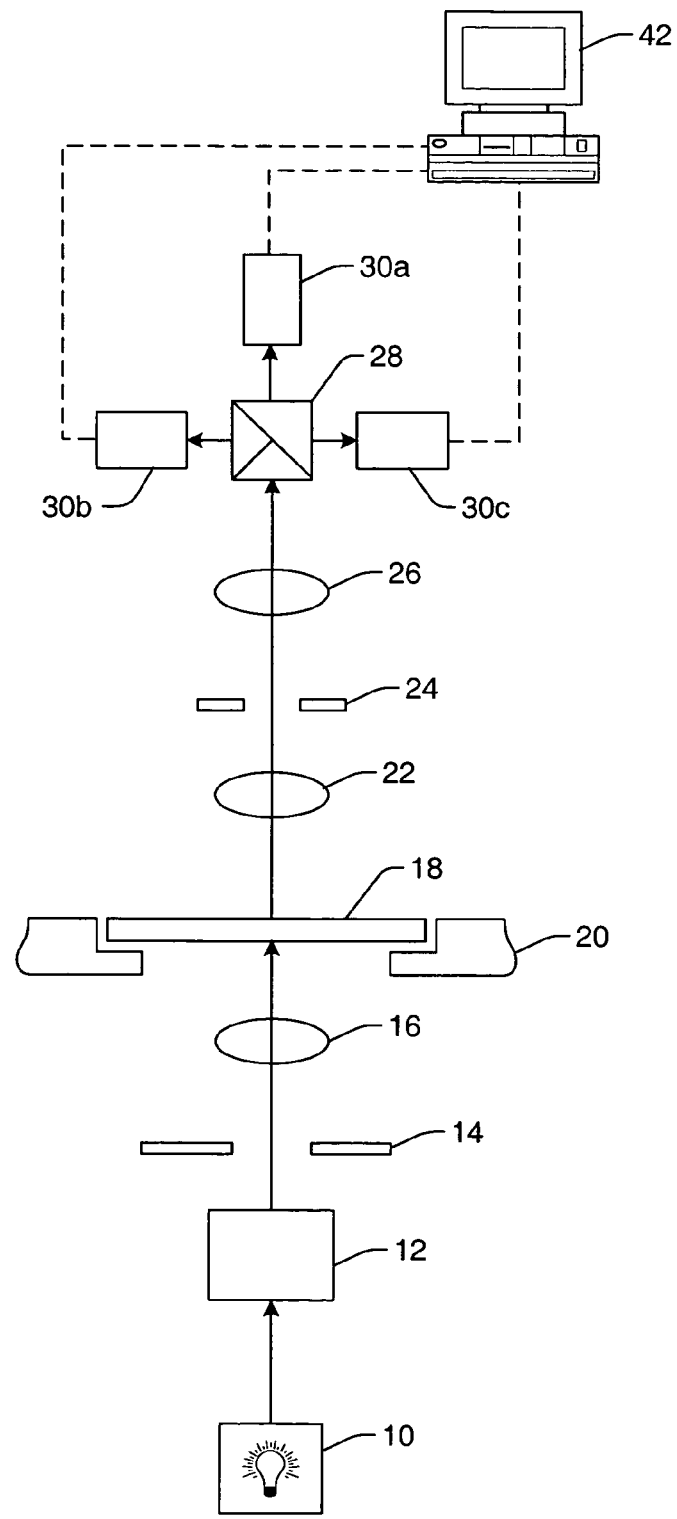
FIGS. 1 and 2 depict schematic diagrams of a side view of various embodiments of a system configured to inspect a reticle.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "reticle" is used to refer to a reticle or a mask. The term reticle may also refer to different types of reticle including, but not limited to, a clear-field reticle, a dark-field reticle, a binary reticle, a phase-shift mask (PSM), an alternating PSM, an attenuated or halftone PSM, and a ternary attenuated PSM, which are described in more detail above. A reticle, as described herein, may or may not include a pellicle. The term reticle may also be used to refer to a reticle that includes optical proximity correction (OPC) features. OPC features are designed to reduce distortions of an image printed using the reticle by reducing optical proximity effects. The term "optical proximity effects" generally refers to variations in lateral dimensions of printed features due to the proximity of other features on the reticle. Such effects may be reduced by determining the distortions due to the optical proximity effects and altering the features on the reticle to compensate for such distortions. Optical proximity effects also refer to corner rounding and general distortion of feature shape caused by the inability of a lens of an exposure system to resolve details smaller than the diffraction limit of the lens. To reduce the distortions caused by such optical proximity effects, secondary, sub-resolutions patterns (commonly referred to as "serifs") may be added to the primary feature patterns. For example, by adding sub-resolution patterns to the corners of a gate pattern, a printed image of the pattern may have less corner rounding than a printed image of the pattern without the sub-resolutions pattern. OPC features may also include incremental linewidth changes to a pattern (commonly referred to as "line jogs") to reduce the distortion of a feature of which a first portion may be isolated from other features on the reticle and a second portion may be proximate other features on the reticle.

As used herein, the term "exposure system" generally refers to any lithography system that prints images of a reticle onto a specimen using light. The exposure system may be a scanning projection system or a step-and-repeat system, or a "stepper." The exposure system may include any exposure system known in the art such as systems commercially available from GCA Corporation, Nikon, ASM Lithography, Canon, SVG Lithography, or Integrated Solutions, Inc.

As used herein, the term "specimen" generally refers to a transparent substrate such as glass, borosilicate glass, and fused silica having a layer of opaque material formed thereon. A specimen may include additional materials formed under the opaque material such as an adhesion layer. In addition, a specimen may include additional materials formed on top of the opaque material such as a bottom anti-reflective coating, a resist (or "photoresist"), and a top anti-reflective layer.

Turning now to the drawings, FIG. 1 illustrates an embodiment of a system configured to inspect a reticle. The system may include an optical subsystem coupled to a processor. The optical subsystem may include an illumination subsystem and a collection subsystem as described in more detail herein. The illumination subsystem includes light source 10. Light source 10 may be a coherent light source such as a laser. The light source may be configured to emit monochromatic light having a wavelength of about 248 nm, about 193 nm, about 157 nm, or another ultraviolet wavelength. Alternatively, the light source may be configured to emit light have a range of wavelengths and may be coupled to a spectral filter (not shown). An example of a broadband light source includes, but is not limited to, a He-Xe arc lamp that generates light in the deep ultraviolet wavelength regime. In this manner, the light source and the filter may emit monochromatic light having a wavelength as described above. The light source and the filter may be configured such that different wavelengths of light may be emitted from the light source and the filter depending upon, for example, the type of reticle being inspected or the type of inspection or measurement being performed. The light source may also be configured to emit light other than ultraviolet light. In addition, the light source may be configured to emit light continuously or at various time intervals in pulses.

The illumination subsystem may also include a number of optical components coupled to the light source. For example, light from light source 10 may first pass through homogenizer 12. Homogenizer 12 may be configured to reduce speckle of the light from the light source. The illumination subsystem may also include aperture 14. Aperture 14 may have an adjustable numerical aperture. For example, the aperture may be coupled to a control mechanism that may be configured to mechanically alter the aperture depending upon a control signal received from a user or from program instructions received from a program recipe being run on the system. In this manner, the light may have various partial coherence factors, σ. For example, aperture 14 may be altered to adjust a pupil of condenser lens 16. The pupil of the condenser lens controls the numerical aperture of the system. As the pupil of the condenser is reduced, coherence of the illumination increases thereby decreasing the value of σ. The value of σ may be expressed as the ratio of the numerical aperture of the condenser lens to the numerical aperture of the objective lens. Exposure systems may have a value of σ in a range between about 0.3 to about 0.9. Therefore, aperture 14 may be altered such that the inspection system has a value of σ between about 0.3 and about 0.9. The value of a may be altered depending upon the features being printed onto a specimen or inspected. For example, a higher value for σ may be used if the reticle includes lines and spaces than if the reticle includes contact holes. The control mechanism may also be configured to alter the aperture to provide annular or off-axis illumination. The aperture may also be configured to provide other types of illumination such as quadrapole or dipolar illumination. The aperture may be further configured to alter a shape of the beam of light. For example, the aperture may be a diffraction optical element or an apodization aperture.

The illumination subsystem may also include a number of additional optical components (not shown). For example, the illumination subsystem may also include a telescope configured to alter the beam diameter of the light. In addition, the illumination subsystem may include one or more relay lenses, additional lenses such as a field lens, folding mirrors, additional apertures, and beamsplitters.

The illumination subsystem may also include condenser lens 16. Condenser lens 16 may be configured to alter a diameter of the light in the object (reticle) plane to approximately, or greater than, the field of view of the system. Light exiting the condenser lens may illuminate reticle 18 supported upon stage 20. The stage is configured to support the reticle by contacting the reticle proximate outer lateral edges of the reticle. An opening in the stage is provided to allow light from the illumination subsystem to illuminate the reticle. Stage 20 may be configured to move the reticle such that an alignment of the reticle may be altered and such that light may scan across the reticle. Alternatively, the illumination system may include a scanning element (not shown) such as an acousto-optical deflector or a mechanical scanning assembly such that the reticle may remain substantially stationary while the light is scanned across the reticle. Stage 20 may also be configured to move the reticle through focus thereby altering a focus setting of the system. The stage may also be coupled to an autofocusing device (not shown) that is configured to alter a position of the stage thereby altering a position of the reticle to maintain a focus setting of the system during an inspection. Alternatively, an autofocusing device may be coupled to the objective lens to alter a position of the objective lens to maintain the focus setting during an inspection.

The system may also include a number of optical components arranged to form a collection subsystem. For example, the collection subsystem includes objective lens 22. Light transmitted by the reticle is collected by objective lens 22. The collection subsystem also includes aperture 24 having an adjustable numerical aperture. The numerical aperture of aperture 24 may also be selected such that light exiting the aperture has a selected magnification. Aperture 24 is positioned between objective lens 22 and lens 26, which may be configured as a tube lens. Light from lens 26 may be directed to beamsplitter 28. Beamsplitter 28 may be configured to direct the light to three detectors 30a, 30b, and 30c. The collection subsystem may also include a number of additional optical components (not shown) such as a magnification lens. The magnification lens may be positioned between lens 26 and the beamsplitter.

Detectors 30a, 30b, and 30c may be configured to form an image of the light transmitted by an illuminated portion of the reticle. Such an image may be referred to as an "aerial image." The detectors should also be sensitive to at least one of the wavelengths of light described above. The detectors, however, may also be sensitive to a range of wavelengths in the deep ultraviolet regime in addition to wavelengths in other regimes. The detectors may include, for example, charge-coupled device (CCD) cameras or time delay integration (TDI) cameras. The detectors may also have a one-dimensional or two-dimensional array of pixels. Each of the three detectors may have a different focus setting. In this manner, the three detectors may form images of the reticle at three different focus settings substantially simultaneously. For example, one detector may be substantially in focus, and the other two detectors may be out of focus in opposite directions with respect to the in focus condition. In addition, the system may include any number of such detectors depending on the mechanical or physical constraints of the system.

Alternatively, the system may only include one detector configured to form an image of the specimen. The detector may have a focus setting approximately equal to a focus setting of an exposure system. Images of the reticle at different focus settings may be formed by forming a plurality of images of the reticle and altering the focus setting of the detector after each image is formed. In such an embodiment, beamsplitter 28 would not be necessary to split the light to multiple detectors.

The system may include a number of other components that are not shown in FIG. 1. For example, the system may include a load module, an alignment module, a handler such as a robotic transfer arm, and an environmental control module and may include any such components known in the art.

As described above, the optical subsystem may be configured to form an aerial image of the reticle using a set of exposure conditions. The exposure conditions include, but are not limited to, wavelength of illumination, coherence of illumination, shape of the beam of illumination, numerical aperture, and focus settings. The set of exposure conditions may be selected to be substantially equivalent to exposure conditions used by an exposure system to print an image of the reticle onto a specimen. Therefore, an aerial image formed by the system may be substantially optically equivalent to an image of the reticle that would be printed on a specimen by the exposure system under the set of exposure conditions.

The set of exposure conditions may include exposure conditions within a process window of the exposure system. In this manner, the system may simulate an image of the reticle that would be printed onto the specimen if the exposure system was operating within a process window of the exposure system. As described above, each of the detectors may have different focus settings. The focus setting of each of the detectors may be within a range of focus settings of a process window of an exposure system. For example, a focus setting of one of the detectors may be approximately at an in focus condition of the process window, and focus settings of the other detectors may be approximately at outer limits of a range of focus settings for the process window. The focus settings for each of the detectors may also be altered depending upon the process window by altering a position of the detectors using, for example, a mechanical device.

As used herein, the term "process window" refers to a range of values for parameters such as focus and dose settings of the exposure system at which the exposure system will print various features of the reticle onto a specimen within process control limitations. The process control limitations may include a range of values for various properties of the printed features such as linewidth, diameter, height and profile characteristics such as corner rounding, top rounding, roughness, and sidewall angle. A process window for focus and dose settings varies depending upon other exposure conditions such as numerical aperture, coherence of illumination, and wavelength and reticle characteristics such as feature size and spatial frequency of the features.

Figure 2:
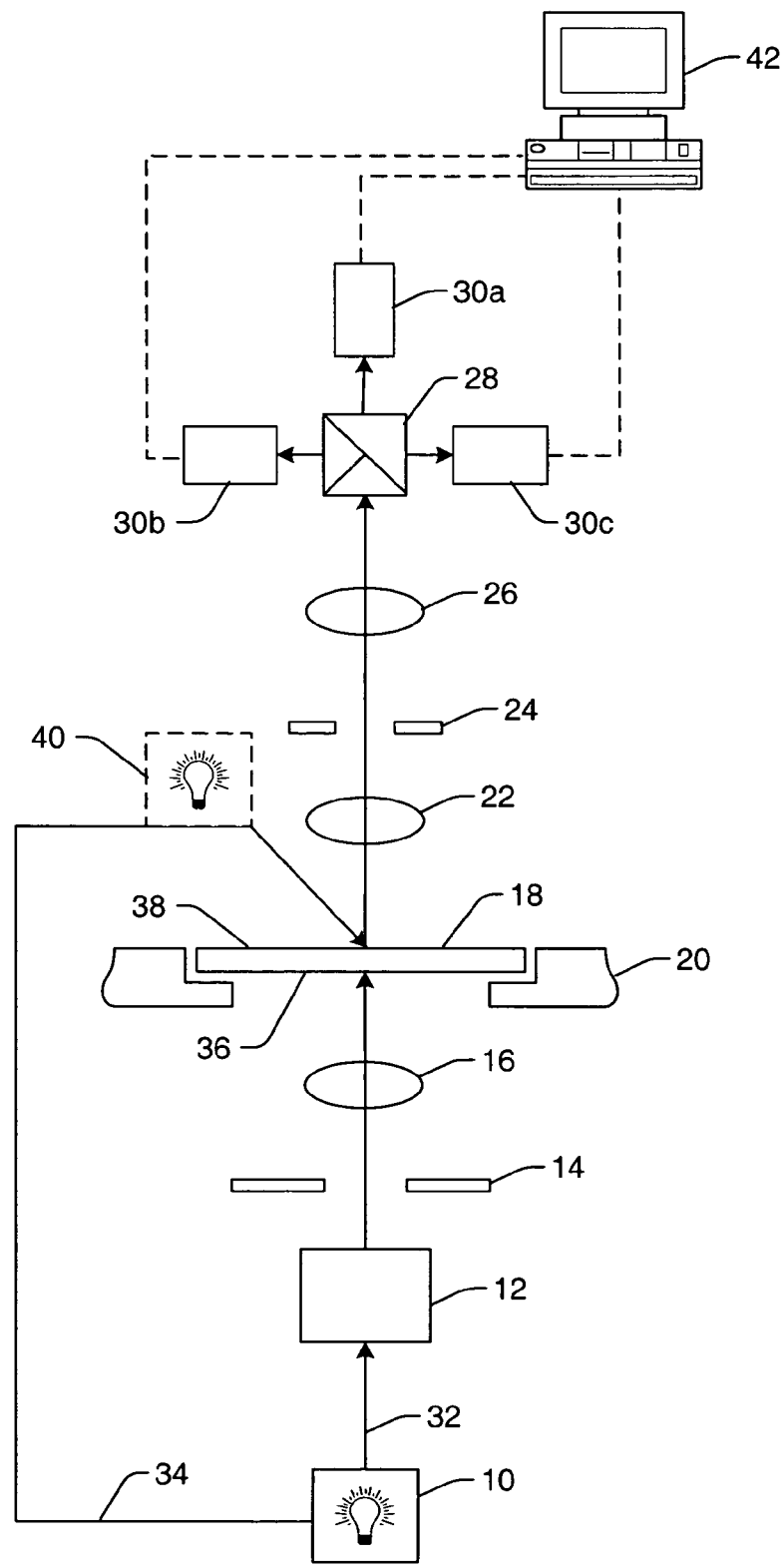

FIG. 2 illustrates an additional embodiment of a system configured to inspect a reticle. The system includes an optical subsystem that may include an illumination subsystem and a collection subsystem as described above. Elements shown in both FIGS. 1 and 2 that may be similarly configured have been indicated using the same reference numerals. As shown in FIG. 2, light source 10 may be configured to illuminate both sides of the reticle. For example, light emitted from light source 10 may be split into paths 32 and 34 by a beamsplitter. Optical components coupled to light source as described above direct the light to side 36 of the reticle. Optical components (not shown) arranged along path 34 such as folding mirrors may direct the light to side 38 of the reticle. As shown in FIG. 2, path 34 may be arranged such that the light is directed to side 38 without passing through any of the components of the collection subsystem. Alternatively, path 34 may be arranged such that the light is directed to side 38 of the reticle by passing through one or more components of the collection subsystem such as objective 22 and/or aperture 24.

In an alternative embodiment, the system may include additional light source 40. The additional light source may be configured to direct light to side 38 of the reticle. The additional light source may be arranged such that the light may be directed to side 38 of the reticle with or without passing through one or more components of the collection subsystem as described above. Such an embodiment would provide additional flexibility in the type of inspections that are performed. For example, light source 10 and additional light source 40 may be configured to emit light having similar characteristics such as wavelength and polarization. Alternatively, the light sources may be configured to emit light having different wavelengths and/or polarizations. In this manner, light from path 32 transmitted by the reticle and light from path 34 reflected from the reticle may be collected simultaneously and detected separately due to their different characteristics.

Light reflected from the reticle may pass through the same optical components of the collection subsystem as the light transmitted by the reticle. For example, light reflected from the reticle may pass through objective lens 22, aperture 24, lens 26, and beamsplitter 28. The light reflected from the reticle may be detected by at least one of detectors 30a, 30b, and 30c. In this manner, the light reflected from the reticle and the light transmitted by the reticle may be detected sequentially. Alternatively, the system may include an additional detector (not shown) that may be dedicated to detecting the light reflected from the reticle. As such, the optical subsystem may detect light reflected from the reticle and light transmitted by the reticle substantially simultaneously.

The systems described herein may also be configured to focus light from the light sources to a plurality of spatially separated spots on the reticle. The system may be further configured to detect light transmitted or reflected from the plurality of spots. Such a system may be configured as described and illustrated in U.S. patent application Serial No. entitled "Multiple Beam Inspection Apparatus and Method," by Kvamme et al., which is incorporated by reference as if fully set forth herein. The systems described herein may be further configured as illustrated and described by Kvamme et al.

The system may also include processor 42, as shown in FIGS. 1 and 2. Processor 42 may be configured to receive image data from detectors 30a, 30b, and 30c. The image data may include images formed from light reflected and/or transmitted by the reticle. Processor 42 may also be configured to detect defects on the reticle from the image data. For example, the processor may be configured to perform a number of functions on the image data such as, but not limited to, altering the data to reduce the effects of distortion, alignment error, illumination non-uniformities, and/or detector non-uniformities. In addition, the processor may compare an aerial image formed using image data from one of the detectors to a reference image stored in a database. The processor may also compare an aerial image formed using light reflected from the reticle to an aerial image formed using light transmitted by the reticle. Either comparison may involve comparing a number of properties of the aerial image to the reference image such as intensity, phase, feature edge position, a dimension of the feature, and an area of the feature. Alternatively, the processor may send the image data to a different processor (not shown) configured to generate the aerial image and to detect defects on the reticle using the image data after the functions described above have been performed. Examples of an appropriate processor include, but are not limited to, a Silicon Graphics 0–200 computer available from Silicon Graphics, Mountain View, Calif., an HP735 workstation available from Hewlett Packard, Palo Alto, Calif., and a Sun SPARC or Sun ULTRASPARC system available from Sun Microsystems, Sunnyvale, Calif. The processor may be further configured as described herein.

If the reticle includes OPC features, the OPC features will not be imaged in the aerial image because the OPC features are smaller than the resolution capability of the aerial inspection system. In contrast, non-aerial imaging reticle inspection systems will image the OPC features on a reticle. For example, non-aerial imaging reticle inspection systems typically have a resolution that is greater than a resolution of an aerial inspection system by about 300% to about 400%. Therefore, the non-aerial imaging reticle inspection systems can image OPC features, which are below the resolution capability of the aerial inspection system. An aerial inspection system has a lower resolution capability because the aerial inspection system is configured to form an aerial image using exposure conditions substantially equivalent to exposure conditions used by an exposure system to print an image of the reticle onto a specimen. Therefore, the aerial inspection system will have a resolution capability approximately equal to the resolution capability of the exposure system. Therefore, an aerial inspection system, as described herein, will form an aerial image of the reticle that does not include images of the OPC features.

Figure 3:
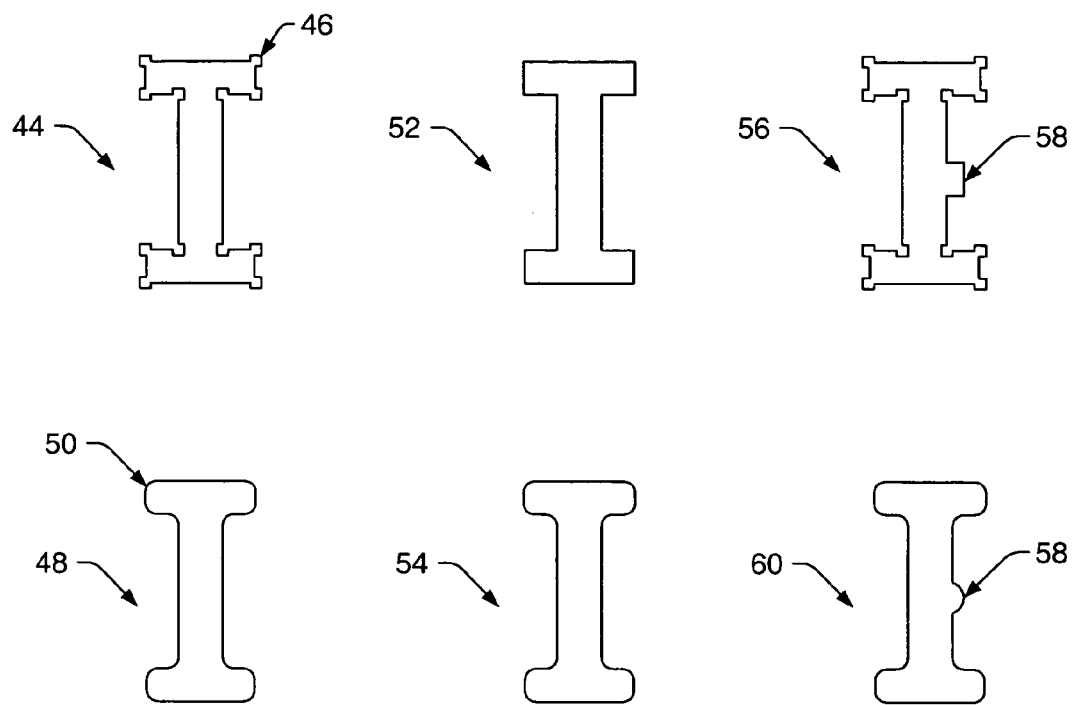
FIG. 3 depicts schematic diagrams of a plan view of various features formed on a reticle and aerial image of the features formed by an exposure system and an inspection system.

In one example, FIG. 3 illustrates a plan view of feature 44 as formed on a reticle that includes OPC features 46, which are sub-resolution features configured to reduce distortions such as corner rounding caused by optical proximity effects. FIG. 3 also illustrates a plan view of aerial image 48 of feature 44 formed by an inspection system configured as described herein. As shown in FIG. 3, OPC features 46 are not imaged in aerial image 48. The aerial image may also include distortions caused by the resolution capability limitations of the inspection system. For example, aerial image 48 may include optical proximity effects such as rounding of corners 50, variations in lateral dimension, general distortion of feature shape, incremental linewidth changes to a pattern, and line edge shortening. An exposure system may also form aerial image 48 of feature 44 because the exposure system may use exposure conditions to print an image of feature 44 onto a specimen, which are substantially equivalent to exposure conditions of the inspection system.

The reference image is substantially equivalent to an image of the reticle that would be printed on a specimen by an exposure system under the set of exposure conditions. The reference image does not include images of the optical proximity features. In contrast, reference images currently used for reticle inspection generally include images of the OPC features because current reticle inspection systems are typically relatively high resolution systems that can resolve features below the resolution capability of an exposure system as described above. Therefore, if currently used reference images are used to detect defects in an aerial image, defects would be detected for every OPC feature included in the reference image and not imaged in the aerial image. Comparing the aerial image to a reference image that does not include images of the optical proximity features, however, would reduce the detection of such defects.

As shown in a plan view of FIG. 3, for example, feature 52 is equivalent to feature 44 as the feature would be formed on a reticle without the OPC features. FIG. 3 also illustrates a plan view of aerial image 54 of feature 52 that would be formed by an exposure system. As shown in FIG. 3, aerial image 54 does not include images of the OPC features. Aerial image 54 may be included in the reference image and may be compared to aerial image 48 formed by the inspection system to detect defects on the reticle. Such a comparison would, therefore, yield a determination that there are no substantial differences between aerial image 48 and aerial image 54 and that feature 44 does not have any defects.

Any discrepancy between the aerial image and the reference image, however, may indicate a potential defect on the reticle. For example, FIG. 3 further illustrates a plan view of feature 56 as formed on a reticle. Feature 56 is equivalent to feature 44, but feature 56 includes defect 58. Defect 58 may be, for example, extra chrome formed on the reticle and abutting feature 56. An aerial image of feature 56 formed by the inspection system described herein may be approximately equivalent to aerial image 60, as shown in FIG. 3. Therefore, if aerial image 60 formed by the inspection system is compared to aerial image 54 of the reference image, defect 58 will be detected by the processor. Although a comparison of an aerial image and a reference image of only one feature is described above, it is to be understood that such comparisons may also be made for only a portion of a single feature, a plurality of features, a portion of the reticle such as a die, or even the entire reticle.

As described above, OPC features will not be imaged in an aerial image formed by the inspection system. Therefore, comparing the aerial image to a reference image that does not include images of the OPC features will reduce, or even eliminate, the detection of nuisance defects. For example, nuisance defects will not be detected because both aerial image 48 formed by the inspection system and aerial image 54 of the reference image do not include images of the OPC features. As used herein, the term "nuisance defects" generally refers to differences between the aerial image and the reference image or another image being compared to the aerial image which are caused by marginalities in the system (or the inspection method) or the processor (or the detection method) not by actual defects. As described above, the detection of nuisance defects is substantially reduced by the embodiments described herein. Therefore, a substantial portion of the defects detected by the system includes defects that would be printed onto the specimen by the exposure system using the reticle under the set of exposure conditions.

Comparing an image of a reticle generated by an inspection system to a reference image is commonly referred to as die-to-database (die:database) inspection. In contrast, an image of a portion of a reticle may be compared to an image of another portion of the reticle to detect defects on one of the portions of the reticle. Such inspection is commonly referred to as die-to-die (die:die) inspection. Certain types of defects are better detected in a die-to-database comparison. For example, repeating defects may be detected using die-to-database comparison but not a die-to-die comparison. In addition, errors made in converting data from a format of a circuit pattern database to the reticle pattern may also be detected using die-to-database comparison but not a die-to-die comparison. Therefore, die-to-database inspection is very useful, and may be particularly useful to reticle manufacturers.

A database including one or more reference images may be rendered in a number of ways. For example, a reference image may be rendered using data in the circuit pattern database as described herein and a simulation program. An example of an appropriate simulation program includes PROLITH commercially available from KLA-Tencor Corporation, San Jose, Calif., which can simulate optical lithography processes to provide aerial images and three-dimensional representations of a resist pattern that may be formed on a specimen using a specific reticle and an exposure system having specific exposure conditions. In addition, any other simulation program known in the art may be used to generate a reference image as described herein. The processor may be configured to access the database and to select one of the reference images to be used for defect detection based on the reticle being inspected and the set of exposure conditions used to expose the reticle.

For relatively high resolution inspection systems, a reference image may be substantially equivalent to a layout of the reticle represented by data in the circuit pattern database because the image of the reticle formed by such inspection systems has basically the same features as the layout of the reticle as described above. For example, such inspection systems may image OPC features. In an embodiment, however, OPC features may be removed from the data representing a layout of the reticle prior to forming the reference image, as shown by feature 52 of FIG. 3. In an alternative embodiment, data representing a layout of the reticle before OPC features are added to the layout of the reticle may be used to form the reference image. In an additional embodiment, the data representing the layout of the reticle may be modified to account for the relatively low resolution of an aerial inspection system, as shown by aerial image 54 of FIG. 3. For example, the data may be modified to round corners of features in the layout, and a filter may be used to compensate for optical parameters of the aerial inspection system. In addition, a full optical system model may be used to model optical parameters of the aerial inspection system to generate a reference image for comparison with an aerial image generated by the aerial inspection system.

In another embodiment, the reference image may also be substantially optically equivalent to an image of the reticle generated from a pattern selected to be formed in a resist. For example, the selected pattern may be a pattern formed in the resist after development or etch of the resist, which is selected by a semiconductor manufacturer. The semiconductor manufacturer may select such a pattern based on characteristics and features of devices that are to be formed using the patterned resist as a mask. For example, the patterned resist may be used as a mask for processes such as ion implantation and etch of a material underlying the resist such as dielectric and conductive materials. Therefore, the pattern selected by the semiconductor manufacturer may be used to determine the aerial image that would produce the selected pattern in the resist. Such an aerial image may be substantially different than the layout of the reticle in the circuit pattern database. For example, OPC features would not be visible in an aerial image printed onto a specimen by an exposure system. In addition, parameters of the exposure system would alter characteristics of features of the reticle as printed on a resist. For example, the exposure system may print an aerial image of the reticle in which corners of features of the reticle are rounded and dimensions of the features are different in comparison to characteristics of the features in the layout of the reticle.

Models that can be used to determine a patterned resist that would be formed by an aerial image and an aerial image that could be used to produce a selected patterned resist are known in the art and several examples are described above. For example, such models may use parameters of a reticle and an exposure system to generate an aerial image that may be printed onto a resist and parameters of the resist and the litho process (i.e., post exposure bake parameters and develop parameters) to generate a pattern that may be formed in the resist with the aerial image. If the pattern selected by the semiconductor manufacturer is a patterned and etched resist, such models may also use parameters of an etch process to generate a pattern that would be formed in the resist with the aerial image. The optical parameters of an aerial inspection system, as described herein, may be configured to be substantially equivalent to optical parameters of an exposure system. In this manner, a comparison of an aerial image generated by the aerial inspection system and a reference image generated as described above may be used to detect differences between the aerial image and an image that if printed onto a resist would produce a selected pattern in a resist. The differences, therefore, may indicate defects on the reticle that would produce defects in a patterned resist. As such, the detected defects may include defects that are meaningful to the semiconductor manufacturer. In addition, defects that are not meaningful to the semiconductor manufacturer may not be detected thereby reducing the detection of nuisance defects and reducing the complexity of analyzing the detected defects.

The processor may also be configured to alter an aerial image formed by the exposure system to simulate performance characteristics of the exposure system and the specimen. For example, a simulation program such as PROLITH as described above may be used to alter the aerial image. Such a simulation program may be combined with other software configured to define model parameters. An example of such software includes the Klarity™ ProDATA AutoTune™ module commercially available from KLA-Tencor. Such software may use experimental data such as an aerial image of a reticle formed by an inspection system as described herein to simulate performance characteristics of the exposure system and the specimen. Such a combination of software provides data-fitting and analysis capabilities with lithography models that are substantially physically correct. Therefore, images that would be printed on a specimen using the reticle and an exposure system may be determined for a variety of resists and exposure conditions using a single aerial image of the reticle formed by an inspection system as described herein.

Such a method reduces the number of aerial images of the reticle that would have to be formed by the inspection system to determine images of the reticle that would be printed by the exposure system at the various levels of a parameter. In addition, such a method would account for properties and variations in the resist that may not be accounted for by the inspection system. Furthermore, the aerial images may be used to analyze various properties of an image of the reticle that would be printed onto a specimen. For example, an aerial image as described herein may be used to determine various properties of features that would be printed onto a specimen such as linewidth, diameter, height and profile characteristics such as corner rounding, top rounding, roughness, and sidewall angle.

Processor 42 may also be configured to control additional components of the system. For example, processor 42 may also be coupled to and configured to control additional components of the system such as light source 10, aperture 14, stage 20, aperture 24, and detectors 30a, 30b, and 30c. In this manner, the processor may alter a parameter of various components of the system to set the exposure conditions under which the reticle is inspected. For example, the processor may alter a parameter of the light source, aperture 14, aperture 24 and a focus setting of one of the detectors such that the exposure conditions of the inspection system are substantially equivalent to the exposure conditions of an exposure system used for imaging of the reticle onto a specimen. In this manner, the system may form an aerial image of the reticle that would be substantially equivalent to an image of the reticle printed onto the specimen by the exposure system.

Furthermore, because various parameters of the optical components may be altered, the optical subsystem may be used to form a plurality of aerial images of the reticle using different exposure conditions of an exposure system. For example, as described above, a mechanical device may be used to alter a position of the detectors to alter a focus setting of the detectors. The processor may be coupled to the mechanical device and may be configured to control the mechanical device to alter a position of the detectors and to associate the focus setting of the altered position with image data received from the detectors. Other exposure conditions such as dose settings may also be altered in a similar manner and associated with image data received from the detectors. In this manner, the processor may detect defects that will be printed onto a specimen by an exposure system using the reticle at different exposure conditions.

A process window for the exposures system may be determined using the aerial images. For example, the process window may include exposure conditions under which aerial images of the reticle may be printed without defects. The defects may be detected using a plurality of reference images of which each reference image may correspond to different exposure conditions. In addition, the processor may analyze the plurality of images to determine a process window of the exposure system using the plurality of aerial images. For example, the process window may be determined by analyzing properties of printed features of the aerial images as described above and determining the exposure conditions that yielded printed features having properties within process control limitations. A process window of the exposure system may also be determined using the aerial image data and a software program such as Klarity Pro-DATA commercially available from KLA-Tencor.

The processor may also be configured to obtain information from several components of the system. For example, the processor may be configured to obtain position data of stage 20 from an interferometer coupled to the stage. Therefore, the processor may associate image data from the detectors with a two-dimensional position on the reticle. The image data may be analyzed, organized and displayed by any suitable means. For example, the data could be grouped across the reticle as a continuous function of spatial position, binned by spatial ranges, binned by exposure system field, by x-y position (or range of x-y positions, such as on a grid), by nearest die, and/or other suitable methods. The variation in image data may be reported by standard deviation from a mean value, the range of values, and/or any other suitable statistical method. The position data may also be received by another controller device of the system. The controller device may use the position data to control one or more parameters of other components of the system such as timing of the light source and the detectors.

The processor may also be configured to output the results of the inspection procedure to a number of modules such as a display medium, a printer, a storage medium, a database, and a fab database. A fab database may include information related to any of the processes performed in a fab such as tool history, wafer history, and reticle history. A fab database may also include any set of data suitable for use in an overall fab management system. An example of such a system is illustrated in PCT Publication No. WO 99/59200 to Lamey et al., which is incorporated by reference as if fully set forth herein.

The defects detected as described herein may be used to determine if the reticle meets qualification criteria. Qualification is a final inspection step that is performed after reticle manufacturing is complete and before the reticle is used to fabricate integrated circuits. Various properties of the detected defects may be used to determine if the reticle meets qualification criteria. For example, the number, dimensions, locations, and/or designations of region or location (which may be determined as described herein) may be compared to predetermined ranges of the various properties set out in the qualification criteria.

Inspection may also be performed periodically after the reticle has been released for semiconductor fabrication to determine if the reticle no longer meets qualification standards. For example, the reticle may be damaged after release by accumulation of particles or other material on the reticle, pellicle damage, and damage caused by electrostatic discharge. Such damage may be sufficient to cause the reticle to fail to meet qualification standards. Example of systems and methods for inspecting a reticle subsequent to qualification are illustrated in U.S. patent application Serial No. entitled "Method for Inspecting a Reticle," to Bareket et al., which is incorporated by reference as if fully set forth herein. The systems and methods described herein may be further configured and may include additional steps, respectively, as illustrated and described by Bareket et al.

If the reticle does not pass qualification, the reticle may be repaired. Due to the time and cost of manufacturing a reticle, defects detected on reticles, and particularly fatal defects, may often be repaired. For example, laser techniques may be used to eliminate unwanted opaque material and pattern protrusions. The laser beam may evaporate the unwanted opaque material. In addition, focused ion beam (FIB) systems may be used to repair reticles, and in particular reticles having relatively small features. FIB systems may be used to remove material from or to add material to the reticle. For example, unwanted opaque material may be removed by sputtering or ion milling the material from the reticle using a focused beam of gallium ions to erode the material. In addition, clear or missing pattern portions may be "patched" with deposited carbon or chrome. Alternatively, a FIB system may be used to locally etch a fine diffraction grating pattern onto the glass surface such that it effectively appears opaque to an exposure system. In another alternative, an opaque material may be deposited onto the reticle using local pyrolytic decomposition of an opaque material-bearing gas at the spot where the opaque material is missing. Decomposition of the gas may be performed by heating the spot on the reticle to a temperature of about 150° C. with an argon laser beam focused through a microscope objective thereby causing the gas to be deposited at the heated spot. Lateral dimensions of the deposited material may be altered by trimming the deposited material with a YAG laser.

The reference image may include designations identifying different types of regions of the reticle, different types of features on the reticle, and/or different portions of features on the reticle. The different types of regions, features, or portions of features may include, for example, critical and non-critical regions, features, or portions of features as described in more detail herein. The designations may vary depending upon a circuit pattern database generated from an integrated circuit design. The integrated circuit design may be developed using any method or system known in the art such as electronic design automation (EDA), computer aided design (CAD), and other integrated circuit design software. Such methods and systems may be used to generate the circuit pattern database from the integrated circuit design. The circuit pattern database includes data representing a plurality of layouts for various layers of the integrated circuit. Data in the circuit pattern database may be used to determine layouts for a plurality of reticles. A layout of a reticle generally includes a plurality of polygons that define features in a pattern on the reticle. Each reticle is used to fabricate one of the various layers of the integrated circuit. The layers of the integrated circuit may include, for example, a junction pattern in a semiconductor substrate, a gate dielectric pattern, a gate electrode pattern, a contact pattern in an interlevel dielectric, and an interconnect pattern on a metallization layer.

A circuit pattern database may include designations as described above. The designations may include, for example, flags or tags associated with different types of regions, features, or portions of features. The designations, however, may include any identification suitable to distinguish one type of region, feature, or portion of a feature from another type. Each region, feature, or portion of a feature or only a portion of the regions, features, or portion of features on the reticle may be associated with a designation. Data in the circuit pattern database representing a layout of reticle may be separate from data in the circuit pattern database representing the designations. In addition, different types of designations may be separated in the circuit pattern database. For example, the circuit pattern database may include a first set of data that includes designations for critical regions, features, or portions of features on the reticle and a second set of data that includes designations for non-critical regions, features, or portions of features on the reticle. Alternatively, different designations may be combined into a single set of data. Data representing a layout of a reticle and designations may have any form readable by a processor coupled to an inspection system or a process tool. For example, the data may include files or other readable data including one or more features and spatial positions within the reticle associated with the features. Each feature may also include one or more polygons or other shapes as described herein and a spatial position within the reticle may also be associated within each of the polygons or shapes. Therefore, the data can be used to fabricate a reticle.

Data in the circuit pattern database representing a layout of reticle may be used to generate a reference image as described herein. The reference image is an image that would be formed on a specimen using a specific reticle and an exposure system having specific exposure conditions if the reticle did not include any printable defects. In addition, the reference image is substantially equivalent to an image of the reticle that would be formed on a specimen by an exposure system under the set of exposure conditions. The reference image does not include images of the optical proximity correction features. Data representing a reference image of a reticle may have any form readable by a processor coupled to an inspection system or a process tool as described above. One or more sets of data that include designations for different types of regions, features, or portions of features on the reticle may be combined with data representing a reference image. In this manner, a reference image that includes such designations may be used to detect defects on an aerial image generated by an inspection system as described above.

A designation may indicate to the inspection system an inspection method to be performed on a portion of the reticle associated with the designation. Such designations may also be used by an inspection system during inspection of a specimen such as a integrated circuit fabricated using the reticle. In addition, or alternatively, a designation may indicate to a processor one or more functions such as a detection algorithm to be performed on data generated by an inspection system in a portion of the reticle associated with the designation. In this manner, different procedures can be used by the processor to detect defects on the reticle in different portions of the reticle. In a critical region, for example, a designation may indicate a more stringent threshold and/or a particular algorithm that may be used to detect defects. In some instances, the designations may be used to indicate only those regions of the reticle to be inspected or only those regions of the reticle not to be inspected. In addition, multiple designations may be associated with a portion of the reticle, and each designation may indicate a different parameter of the detection procedure. For example, a first and a second designation may be used to indicate a threshold and an algorithm, respectively, that are to be used for detecting defects in a single portion of a reticle. In addition, such designations may also be used by a process tool such as a pattern generator or a reticle writer to indicate to the process tool parameters of a process to be used to fabricate a reticle or an integrated circuit using the reticle.

Figures 4A, 4B, 4C:
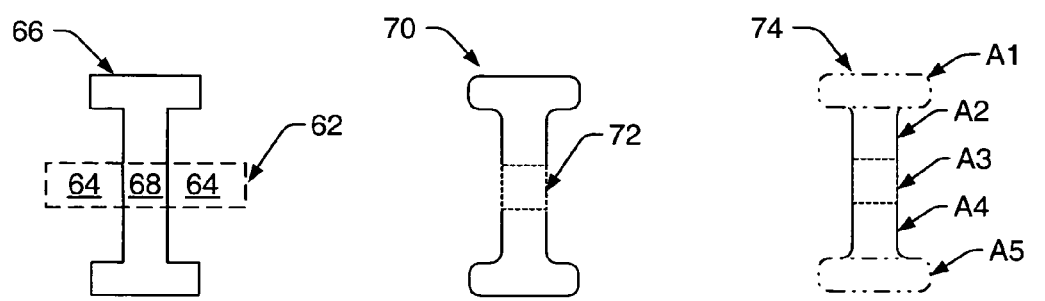
FIG. 4a depicts a top schematic view of an embodiment of two features in layouts of two different reticles represented by data in a circuit pattern database.
FIG. 4b depicts a top schematic view of a feature shown in FIG. 4a that may be included in a reference image.
FIG. 4c depicts a top schematic view of a feature 74 shown in FIG. 4a having 5 different regions associated with one or more designations.

FIG. 4a illustrates a top schematic view of an embodiment of two features in layouts of two different reticles represented by data in a circuit pattern database. The two features are combinable to form at least a part of an element of an integrated circuit fabricated using the reticles. In the example illustrated in FIG. 4a, the element of the integrated circuit is a transistor. For example, feature 62 represents a region of a substrate into which ions are implanted to form a diffusion area of the transistor. Feature 62 includes junction areas 64 of the transistor. A designation may be associated with feature 62 to indicate that feature 62 is a non-critical feature. Feature 66 represents a region of a substrate onto which a layer of conductive material such as polysilicon is formed to form a gate of the transistor. Feature 66 may include gate electrode area 68 of the conductive material layer. A designation may be associated with gate electrode area 68 to indicate that the gate electrode is a critical portion of feature 66. For example, the width of a gate electrode dictates the speed of the integrated circuit. In addition, if the width of a gate electrode is not formed within a small margin or error, then the integrated circuit may not function properly or at all. Therefore, forming a gate electrode having a predetermined width is a critical step in the fabrication of integrated circuits. Designations associated with other portions of feature 66, however, may indicate that these portions are non-critical portions of feature 66. Therefore, feature 66 includes critical and non-critical portions indicated by different designations.

FIG. 4b illustrates a top schematic view of feature 70 that may be included in a reference image as described above. Feature 70 is equivalent to an aerial image of feature 66 of FIG. 4a as it would be printed onto a specimen with distortions due to optical proximity effects. As shown in FIG. 4b, feature 70 includes gate electrode region 72 associated with a designation. The designation may indicate that region 72 is a critical portion of feature 70 as described above. Therefore, a processor using the reference image to detect defects in an aerial image of the reticle may use a different procedure to inspect region 72 as opposed to other regions of the feature. For example, the processor may use a more stringent threshold or a different algorithm to inspect region 72 than other regions of the feature. Data representing the reference image and data representing the designations may be separate but used together during inspection. Alternatively, data representing the reference image and data representing the designations may be combined into a single data set. Although feature 70 is shown to include only one region associated with a designation, it is to be understood that feature 70 may include any number of regions having one or more designations. For example, FIG. 4c illustrates a top schematic view of an embodiment of feature 74 that is equivalent to feature 70 having 5 different regions A1, A2, A3, A4, and A5 associated with various designations.

FIG. 5 illustrates content of an embodiment a database structure that may be used to represent a layout of a reticle. Database structure 76 is shown to include various definitions 78, 80, and 82 for feature 74 as shown in FIG. 4c. Although only one feature is shown in database structure 76, it is to be understood that such a database structure may include definitions for one or more features, definitions for one or more regions on the reticle such as a die, listings of all features or die in a reticle, and one or more reticles that may or may not correspond to an entire set of reticles used to fabricate an integrated circuit. As shown in FIG. 5, each region of the feature included in the various definitions is associated with a spatial position, $(x,y)_i$, within the reticle and may or may not be associated with a designation.

As shown in definition 78, designations may be used to distinguish critical regions of a feature from non-critical regions of the feature. Region A3 of feature 74 corresponds to a gate electrode of the feature and is, therefore, a critical region as described above. All other regions A1, A2, A4, and A5 corresponds to non-critical regions of regions. Therefore, in definition 78, region A3 has a different designation than regions A1, A2, A4, and A5, and a different inspection procedure may be used to detect defects in region A3 than in regions A1, A2, A4, and A5. As shown in definition 80, designations may be used to indicate a plurality of different types of regions of the feature. The designations may indicate that different inspection procedures are used for the plurality of different types of regions. For example, the designation associated with region A3 may indicate that a more stringent threshold is used to detect defects in region A3 than in regions A1 and A5. In addition, the designations associated with regions A1 and A5 may indicate that a more stringent threshold is used to detect defects in regions A1 and A5 than in regions A2 and A4. The designations illustrated in definition 80 may also, or alternatively, indicate other parameters of the inspection procedure such as which algorithm is to be used to detect defects in the region of the feature. As illustrated in definition 82, the designations may also include names that indicate a threshold level, an algorithm, or another parameter of an inspection procedure to be used to inspect regions of the feature.

Any processor as described herein may be configured to indicate which defects are detected in critical regions of the reticle or critical regions of features of the reticle. For example, the processor may generate output of the results of the inspection procedure as described above. The results of the output may include a list of defects found on the reticle and various properties of the defects such as location and one or more dimensions of the defects or a summary of the defects grouped by one or more such properties. The processor, however, may also associate a type of region that a defect was found in with the defect based on the designations described above. The processor may include such region type information in the output. In addition, the processor may group the defects based on the types of regions in which the defect was found. In this manner, the output of the inspection system may include information about all defects separated into groups or only a subset of all of the groups of defects.

The types of regions in which defects are found may be used to determine if the reticle passes qualification and/or if further processes are to be performed on the reticle. For example, the processor may indicate which defects were detected in critical regions of the reticle. Defects in the critical regions may be used to determine if the reticle passes qualification. In addition, information about the defects detected in critical regions may be used to determine if the reticle should be repaired or re-processed or if the reticle should be scrapped. Furthermore, the processor may provide information about the defects detected in critical regions, but not in non-critical regions, to a repair tool. In this manner, only defects detected in critical regions may be repaired thereby reducing the time and expense of repairing non-critical defects detected on a reticle. Alternatively, the repair tool may be configured to identify defects detected in critical regions and may only repair these defects.

A system or a method that uses different procedures for inspection or fabrication of a reticle based on the different types of regions within the reticle provides a number of advantages. For example, such an inspection system or method may reduce the time and expense of inspecting a reticle by reducing the stringency used to inspect non-critical regions of the reticle. In addition, the inspection system or method may increase the stringency used to inspect critical regions of the reticle thereby increasing the accuracy of inspection in these regions. In this manner, a system or method as described herein translates the design specifications and tolerances for properties of an integrated circuit such as dimensions of integrated circuit elements from a designer to inspection and/or fabrication of a reticle. A system or method as described herein may also include any of the elements or steps illustrated in U.S. patent application Ser. No. 09/213,744 entitled "Mechanisms for Making and Inspecting Reticles" by Glasser et al., filed on Dec. 17, 1998, and PCT Application No. WO 00/36525 by Glasser et al., which are incorporated by reference as if fully set forth herein. Furthermore, a system or method as described herein that also performs or includes defect detection by comparing an aerial image to a reference image as described above provides detection of a substantial portion of printable defects using the specifications and tolerances determined by an integrated circuit designer.

After defects have been detected on the reticle, the defects are typically reviewed. A defect review system is usually separate from an inspection system. For example, data representing images and properties of the defects generated by an inspection system may be stored on a transportable medium and carried to a processor of a defect review system. The defect review system includes a display system such that a user can view the detected defects. The display system may also be used to display the properties of the detected defects. The defect review system may also include a separate optical subsystem. Therefore, a reticle must be removed from an inspection system after inspection and transported (i.e., by a user) to the defect review system. The optical subsystem may be used to generate additional images of the defects. For example, the optical subsystem may be a relatively high power microscope configured to generate an image of the defect at a magnification higher than that of an inspection system. In this manner, a user may view greater detail of the defect than is provided by the images generated by the inspection system. The defect review system may include other analytical subsystems such as a scanning electron microscope in addition to or as an alternative to the optical subsystem. Such analytical subsystems may also be used to generate additional images or data of the defects.

A defect review system as described above, however, requires space in a clean room and facilities separate from the space and facilities needed for the inspection system. Therefore, the cost of operation of a separate defect review system and inspection system may be approximately twice that of the inspection system alone. In addition, a separate defect review system and inspection system may each include several of the same components such as a power supply, processors, load modules, alignment modules, environmental control units, and mechanical components such as vibration control units and robotic handlers. As such, the capital cost of a defect review system may be approximately the same as or greater than the capital cost of an inspection system.

Furthermore, a reticle must be transferred from an inspection system to a separate defect review system. In this manner, the reticle may be exposed to additional contaminants or damage caused by, for example, particles and electrostatic discharge, respectively. In addition, the time required for overall inspection and review may be increased significantly by the time required to transport the reticle, to load the reticle in the defect review system, and to align the reticle prior to defect review. Therefore, an inspection system and a separate defect review system may have several disadvantages although defect review generally cannot be eliminated from the overall reticle inspection process.

In an embodiment, a system configured to inspect a reticle may include an inspection subsystem coupled to a review subsystem as described in more detail below. The inspection subsystem may be configured to form a first aerial image of the reticle. The first aerial image can be used to detect defects on the reticle. The review subsystem may be configured to form a second aerial image of the reticle. The second aerial image can be used to analyze the defects. Such a system provides improved reticle inspection and defect review in a cost efficient manner. For example, the inspection and review subsystems may be combined into a single system. Therefore, the combined inspection and review system would have a reduced cost of ownership compared to separate inspection and defect review systems. In addition, a combined inspection and review system would reduce handling of the reticle. For example, the reticle can be loaded into the combined system prior to inspection and would not have to be removed from the system until after defect review.

A system having inspection and defect review capability may be configured as shown in FIG. 1 or 2, which are described in detail above. In such a configuration, the inspection subsystem and the defect subsystem may have common optics. For example, the illumination subsystem shown in FIG. 1 or 2 may be used to provide illumination for both the inspection subsystem and the review subsystem. In addition, the collection subsystem shown in FIG. 1 or 2 may be used to generate an aerial image of the reticle for both inspection and defect review.

A parameter of one or more optical components of the illumination or collection subsystem may be altered depending upon whether inspection or defect review is being performed. For example, a wavelength of light source 10, a numerical aperture of aperture 14, a magnification of a magnification lens, and/or a focus setting of one or more of detectors 30a, 30b, and 30c may be altered between inspection and defect review. In addition, a parameter of one or more of the optical components may be altered a number of times during defect review. For example, a focus setting of one or more of detectors 30a, 30b, and 30c may be altered a number of times during defect review such that a number of aerial images may be formed of a detected defect. In this manner, the review subsystem may generate a greater amount of information about a defect than an inspection system, and such information may be used to further characterize the defect and/or performance an exposure system. For example, such information may be used to further characterize printability of the defect and/or a process window of the exposure system. A parameter of such optical components may be altered by a processor as described above.

In an alternative embodiment, the system shown in FIGS. 1 and 2 may be altered to include additional optical components (not shown) that may be used in place of optical components shown in these figures. For example, the system may include an additional detector that may be inserted into the system in place of one or more of detectors 30a, 30b, and 30c before defect review. Additionally, or alternatively, an additional light source, condenser lens, objective lens, and/or lens may be included in the system and may be used in place of light source 10, condenser lens 16, objective lens 22, and lens 26, respectively, for defect review. In addition, the system shown in FIGS. 1 and 2 may be altered to include an entire additional illumination subsystem or an entire additional collection subsystem. Therefore, between inspection and defect review, the entire illumination or collection subsystem may be replaced. Replacing one or more optical components or an entire subsystem of the system may be performed by a mechanical device controlled by a processor such as processor 42. As such, the components or subsystems may be switched automatically.

The system may also include a focusing system configured to adjust a focus setting of the individual components and the overall system when a parameter of one or more of the optical components is altered or when one or more of the optical components or subsystems is replaced. For example, an autofocusing device as described above may be coupled to each of the optical components that are configured to be switched between inspection and review and may be configured to alter a focus setting of the optical components after they are switched and before inspection or review is performed. Such an autofocusing device may also be coupled to an illumination subsystem and a collection subsystem such that a focus setting of the subsystem may be altered after an entire subsystem is replaced.

Figure 6:
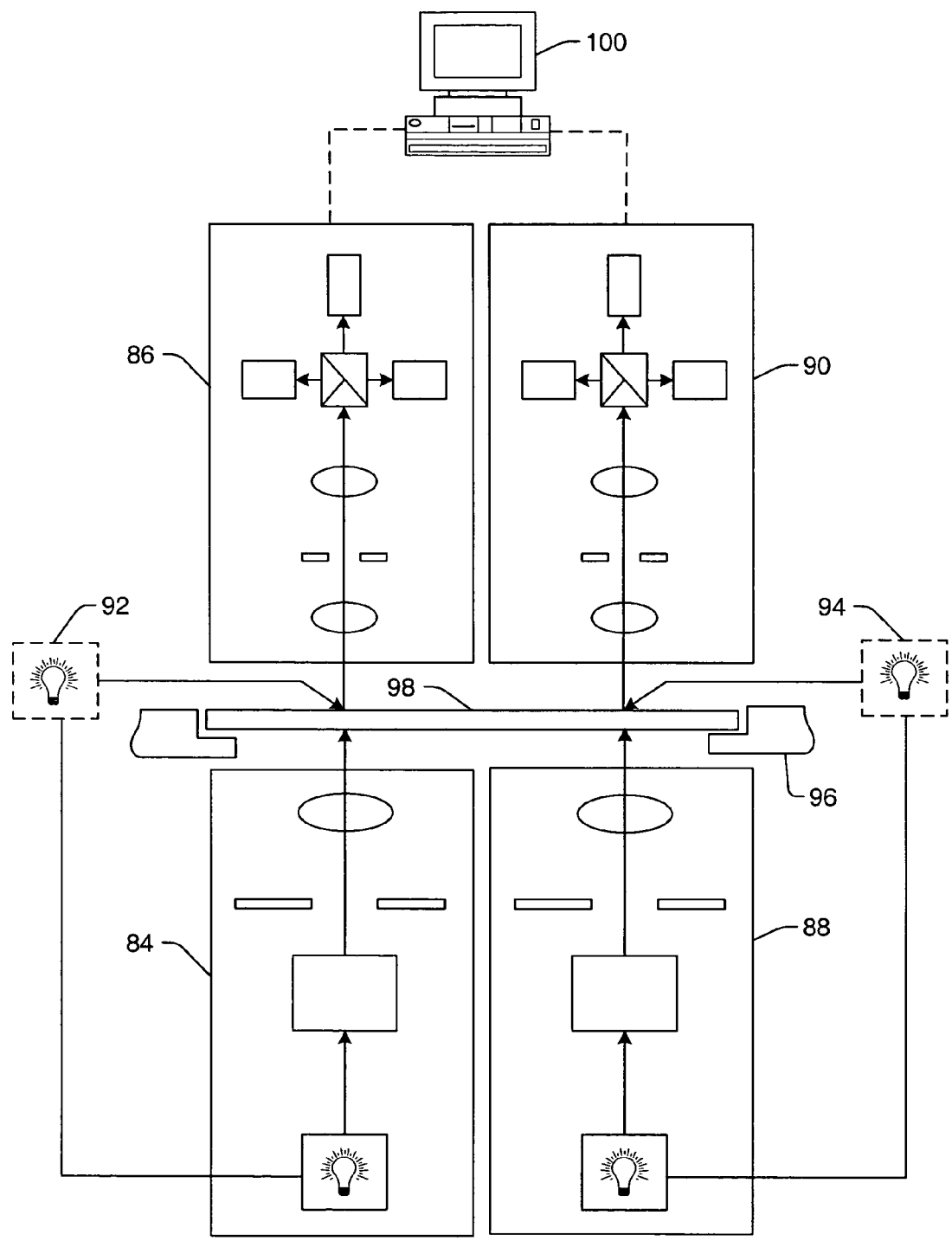
FIGS. 6–8 depict schematic diagrams of side views of various embodiments of a system configured to inspect a reticle that includes an inspection subsystem coupled to a review subsystem.

FIG. 6 illustrates a schematic diagram of a side view of an embodiment of a system configured to inspect a reticle that includes an inspection subsystem coupled to a review subsystem. In this embodiment, the inspection and review subsystems have separate optics and a common stage. For example, inspection subsystem may include illumination subsystem 84 and collection subsystem 86. Review subsystem may include illumination subsystem 88 and collection subsystem 90. The illumination and collection subsystems are shown to include optical components as shown in FIG. 1, and the reference numbers used to indicate the components in FIG. 1 are not included in FIG. 6 for simplicity. The illumination and collection subsystems may also be configured as described with respect to FIG. 1 such that an aerial image of the reticle may be formed for both inspection and review. It is to be understood, however, that the illumination and collection subsystems may be configured according to any of the embodiments as described herein. For example, illumination subsystems 84 and 86 may or may not include additional light sources 92 and 94, respectively, which may be configured as described with respect to FIG. 2. In addition, the inspection subsystem and the review subsystem may include additional optical components (not shown), as described above, that may be used to replace one or more of the optical components shown in FIG. 6. The additional optical components may add flexibility to the subsystems such that various techniques may be used for inspection and review.

The system shown in FIG. 6 also includes common stage 96. Stage 96 may be configured to support reticle 98 and may be further configured as described above. As shown in FIG. 6, the inspection subsystem and the review subsystem may both access a portion of the reticle concurrently. In this manner, inspection and review of the reticle can be performed substantially simultaneously. For example, the inspection subsystem may detect defects on a portion of the reticle while the review subsystem is reviewing defects on a different portion of the reticle. In addition, the inspection subsystem and the review subsystem may be configured to scan the reticle as described above and in series. Therefore, the inspection subsystem and the review subsystem may detect and review defects on a single portion of the reticle in series.

If the inspection and review subsystems do not share a common stage, the processor may have to convert coordinates of the inspection subsystem into coordinates of the review subsystem such that the review subsystem may locate the detected defects for review. Alternatively, if the inspection subsystem and the review subsystem share a common stage, as shown in FIG. 6, the coordinates of the inspection subsystem and the review subsystem may be substantially the same thereby eliminating converting coordinates of one tool into another.

The system may be configured such that if only inspection or review is to be performed on a reticle then only the inspection subsystem or the review subsystem would image the reticle. For example, the inspection and review subsystems may be coupled to a mechanical device such as a stepper motor controlled by a processor, as described herein. The processor may control the mechanical device to move one of the subsystems away from an area of the system occupied by the stage if only inspection or review is to be performed. Alternatively, functionality of one of the subsystems may be reduced, or even turned off, if only inspection or review is to be performed. The system may be further configured according to any of the embodiments described herein.

Collection subsystems 86 and 90 may be coupled to processor 100. Processor 100 may be configured according to any of the embodiments described herein. For example, the processor may be configured to detect defects on the reticle using image data generated by collection subsystem 86. The processor may detect defects on the reticle by comparing the image data to a reference image as described herein. The processor may also be configured to review defects on the reticle using image data generated by collection subsystem 90. In an alternative embodiment, the system may include two processors (not shown), and each processor may be coupled to one of the collection subsystems. The processors may be coupled to each other such that information and/or image data regarding the defects detected and/or reviewed may be shared between the processors. For example, the processors may be coupled by a transmission medium such as a wire, a cable, a wireless transmission path, and/or a network. The transmission medium may include "wired" and "wireless" portions.

Reviewing defects may include performing one or more functions on the image data. The one or more functions may include, but are not limited to, determining a property of the defect such as a dimension, assessing printability of the defect, determining a performance characteristic of an exposure system such as a process window, classifying the defect, and determining a root cause of the defect. The one or more functions that are performed during review may vary, for example, depending upon program instructions received from a user. The processor may be configured to display aerial images of the defects to the user, and the user may select defects to be reviewed and to select functions to be performed for review of the selected defects. Alternatively, the user may select a number of functions to be performed during review of all defects. The functions may be selected by the user at the time of defect review or may be stored in a "recipe" that may be selected by the user. A recipe is commonly used to refer to a set of program instructions that includes information representative of a process to be performed during inspection, review, or any other process. The information may include properties of the specimen being inspected, reviewed, or otherwise processed and program instructions representative of steps selected to be performed on the specimen during inspection, review, or processing. In this manner, defect review may be performed manually or automatically. The processor may be further configured according to any of the embodiments as described herein. For example, the processor may be configured to classify a defect and determine a root cause of a defect according to embodiments described herein.

The one or more functions performed during defect review may also include generating a two-dimensional or three-dimensional map of the reticle. The map may include a plot of the defects detected on the reticle as a function of spatial position on the reticle. The map may include only a subset of the detected defects or all of the detected defects. For example, a map may be generated that includes only defects that were detected in critical regions on the reticle, which may be determined as described herein. Alternatively, the map may include only defects having a lateral dimension within a predetermined range, a particular classification, or a particular cause. Generating a map of only a subset of defects may be used to provide only the defect information about which a user cares to view. For example, a user may only want to see defects in critical areas, having a lateral dimension greater than about 5 mm, classified as missing chrome, and/or caused by incomplete resist coverage during lithography. Processor 100 may be configured to select such defects from all of the detected defects and generate a two- or three-dimensional map of the defects. In addition, or alternatively, the map may include properties of printed features as a function of spatial position on the reticle. The properties may include, for example, lateral dimension of features on the reticle. The map may also include some type of indication for different ranges of the property. The indicia may include color coding, flags, or any other such indicia known in the art. In this manner, the map may illustrate variations in a plot of a property of printed features of the reticle as a function of spatial position of the reticle.

The extent of the within reticle variation (such as the range, standard deviation, and the like) may also be analyzed as a function of process conditions. For example, the within reticle standard deviation of the measured lateral dimension may be analyzed as a function of variation in one or more process conditions such as develop time, exposure conditions, resist thickness, post exposure bake time and/or temperature, pre-exposure bake time and/or temperature, etch parameters, and cleaning parameters. It may also, or instead, be grouped, reported and/or analyzed as a function of within reticle variation in one or more of such processing conditions.

Figure 7:
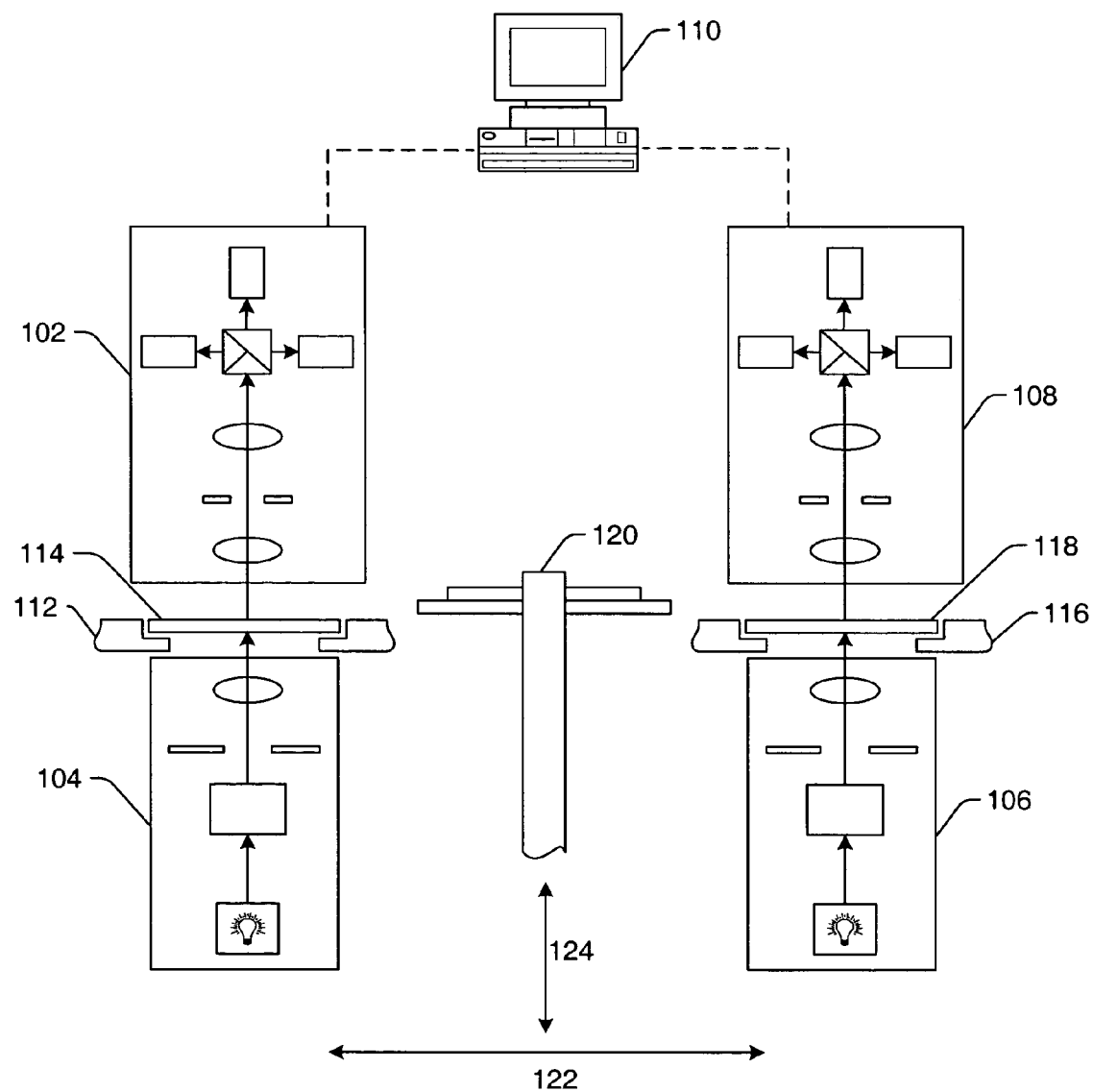

FIG. 7 illustrates a schematic diagram of a side view of an embodiment of a system configured to inspect a reticle that includes an inspection subsystem coupled to a review subsystem. In this embodiment, the inspection and review subsystems have separate stages and a common handler. For example, the inspection subsystem may include illumination subsystem 102 and collection subsystem 104. Review subsystem may include illumination subsystem 106 and collection subsystem 108. Illumination subsystems 102 and 106 and collection subsystems 104 and 108 may be further configured as described with respect to FIG. 6. The system may include processor 110 coupled to at least collection subsystems 104 and 108. The processor may be configured according to any of the embodiments as described herein.

The inspection subsystem includes stage 112 configured to support reticle 114. The review subsystem includes stage 116 configured to support reticle 118. Stages 112 and 116 may be further configured according to any of the embodiments described herein. The system may also include common handler 120. Handler 120 may be configured to remove a reticle from a load module (not shown) of the system. The handler may be also be configured to move the reticle from the load module to a alignment module (not shown). After the reticle has been aligned, the handler may move the reticle to stage 112 or stage 116 depending upon whether inspection or defect review is to be performed on the reticle. Alternatively, the handler may be configured to move the reticle directly from the load module to stage 112 or stage 116 depending upon whether inspection or defect review is to be performed on the reticle. The handler, however, may typically move the reticle from the load module to stage 112 for inspection. After inspection, the handler may be configured to move the reticle along direction 122 from stage 112 to stage 116 such that defect review may be performed on the reticle.

The handler may also be configured to move in a number of other directions. For example, as shown in FIG. 7, the handler may be configured to move in direction 124 such that disposing a reticle onto or removing a reticle from a stage may include lifting the reticle off of the stage to avoid damage to the reticle. In addition, the handler may be configured to rotate and/or move in other lateral directions depending upon an arrangement of the inspection subsystem, the review subsystem, the load module, and the alignment module. The handler may also be coupled to processor 110. Processor 110 may be configured to control the handler depending upon, for example, program instructions received from a user. The handler may include any robotic or mechanical handler known in the art. The load module, the handler, and the inspection and review stages may be further configured as described and illustrated in U.S. Pat. No. 5,980,187 to Verhovsky, which is incorporated by reference as if fully set forth herein. Such a handler may also be included in any of the other embodiments of a system as described herein. The system may also include more than one handler, and each handler may be configured to perform a subset of all of the move operations. The system may be further configured according to any of the embodiments as described herein.

A system that includes an inspection subsystem coupled to a review subsystem that have common optics, separate optics and a common stage, or separate stages and a common handler may provide several advantages over separate inspection and review systems. For example, the reticle does not have to be loaded out of the inspection system, transported to a review system, and loaded into the review system between inspection and review. Therefore, the overall time required for inspection and review may be reduced. In addition, such a system reduces the potential for contamination and/or damage of the reticle because the reticle remains in one system throughout inspection and review and is only transported by a single handler.

In an embodiment, a method for inspecting a reticle may include inspecting the reticle by forming a first aerial image of the reticle while the reticle is disposed in a system. The method may also include detecting defects on the reticle using the first aerial image. In addition, the method may include reviewing the defects by forming a second aerial image of the reticle while the reticle is disposed in the system. The method may further include analyzing the defects using the second aerial image. In an embodiment, inspecting the reticle and reviewing the defects may be performed substantially simultaneously. In a further embodiment, the method may include altering optics of the system between inspection and review. In an additional embodiment, inspecting the reticle and reviewing the defects may be performed while the reticle is disposed upon a common stage of the system. In an alternative embodiment, the method may include moving the reticle from a first stage to a second stage between inspection and review using one handler. The method may further include additional steps of other methods as described herein.

Figure 8:
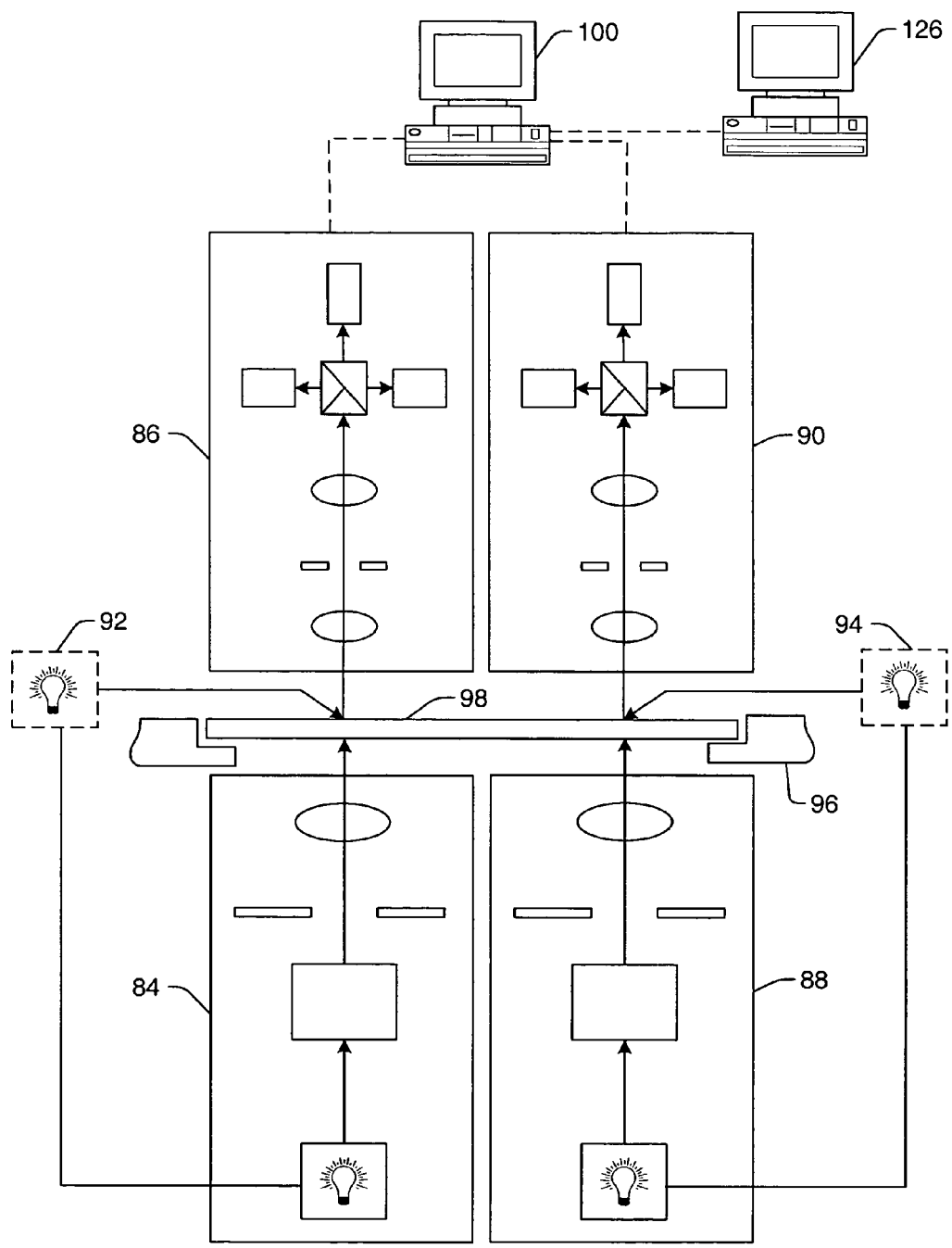

FIG. 8 illustrates a schematic diagram of a side view of an embodiment of a system configured to inspect a reticle that includes an inspection subsystem coupled to a review subsystem. Although the system is configured as described with respect to FIG. 6, it is to be understood that the system may alternatively be configured as described with respect to FIGS. 1, 2, and 7. Elements shown in both FIGS. 6 and 8 that may be similarly configured have been indicated using the same reference numerals. As shown in FIG. 8, the system also includes image computer 126. Image computer 126 may be configured to receive image data from the inspection and review subsystems. For example, image computer 126 may be coupled to processor 100 by a transmission medium such as a wire, a cable, a wireless transmission path, and/or a network. The transmission medium may include "wired" and "wireless" portions. Processor 100 may be coupled to at least collection subsystems 86 and 90 as described above. The image data represents first and second aerial images generated by the inspection and review subsystems, respectively. The system may be further configured according to any of the embodiments as described herein. Such an image computer may also be included in any other embodiments of a system as described herein.

Image computer 126 may be configured to perform one or more functions on the image data. For example, the one or more functions may include detecting defects on a reticle by comparing the image data from the inspection subsystem to a reference image of the reticle stored in a database. The reference image may be a reference image as described above. For example, the reference image may be substantially equivalent to an image of the reticle that would be formed on a specimen by an exposure system under the set of exposure conditions. The reference image does not include images of optical proximity correction features on the reticle. The image computer may also be configured to generate a database including such a reference image. The image computer may render the database, which may include one or more reference images, as described herein. Alternatively, the one or more functions may include detecting defects on a reticle by comparing a first portion of the image data from the inspection subsystem to a second portion of the image data from the inspection subsystem. The first and second portions may include different die on the reticle, and such a comparison is commonly referred to as a die:die comparison.

Image computer 126 may be configured to perform other functions such as detecting defects on the reticle using image data from the inspection subsystem and classifying the defects using image data from the inspection or review subsystem. One embodiment of a method, which the image computer may be configured to use, for classifying defects on a reticle is illustrated in the flow chart of FIG. 9. The method includes receiving input from an inspection system, as shown in step 128. The input may include image data generated by an inspection subsystem or a review subsystem as described herein. As described above, aerial images generated by an inspection or review subsystem may be displayed to a user. The user may view aerial images of all of the detected defects. In addition, the user may view the aerial images of the detected defects arranged by natural grouping. For example, the method may include feature extraction, as shown in optional step 130. The method may also include natural grouping of the aerial images using the extracted features, as shown in optional step 132. The image computer may perform grouping of the defects using any known method in the art. Examples of methods that may be used for grouping of defects include, but are not limited to, the Kohonen mapping technique, a K-means, a method described by N. Otsu in "A Threshold Selection Method from Gray-Level Histograms," IEEE Trans. Systems, Man, and Cybernetics, Vol. SMC-9, 1979, pp. 62–66, which is incorporated by reference as if fully set forth herein. In addition, the image computer may group the defects using invariant core classes. An example of invariant core classes is illustrated in PCT Publication No. WO 00/03234 to Ben-Porath et al., which is incorporated by reference as if fully set forth herein.

The method may include manual classification of the aerial images by the user, as shown in step 134. The user may view and classify the aerial images using the input from the inspection system and optionally the aerial images arranged by natural grouping. The user may assign one or more images into individual groups. The images that are manually classified by the user may be used to classify non-manually classified images generated by inspection or review. For example, the image computer may group the remaining images based on common features with the manually classified images. The user may review the results of the classification of the remaining images. Depending upon the number of images that were incorrectly classified by the image computer, the user may alter the grouping of manually classified images. Altering the grouping of manually classified images may include adding and/or deleting images from one or more of the manually classified groups. The user may also view an algorithm or another function developed by the image computer in response to the manually classified images, which was used to automatically classify the remaining images. In addition, the user may determine how the automatic classification differed from the manual classification. The user may continue to review the results of automatic classification and to alter the manually classified images until the user is satisfied with the automatic classification of the images.

The manual classification of the images that produces a satisfactory automatic classification of the images may be used to automatically classify additional aerial images generated by inspection or review. For example, the method may include feature extraction of the manually classified images, as shown in step 136. Predetermined features of the manually classified images may be extracted by software operable by the image computer. The software may be operable to determine values for a number of features of the manually classified images and to store the values for the features in a data structure. The features may include, but are not limited to, lateral dimensions, brightness, color, shape, roughness, moment of inertia, context, proximity to other defects and/or features, connectivity to proximate defects and/or features, and other characteristics determined from the image such an electrical defect that the defect may cause in an integrated circuit (i.e., open, short) and classification of the defect (i.e., particle, scratch). The features may also include spatial location of the defect on the reticle and a designation associated with a region of the reticle in which the defect is located. Such designations are described in further detail herein.

In addition, the feature may include other information associated with the defect such as results of analytical testing on the defect, information related to the processing of the reticle prior to detection of the defect, and cause of the defect. Analytical testing on the defect may include any analytical technique known in the art. Data regarding metal thickness and its within reticle variation could be derived from an x-ray reflectance tool such as that disclosed in U.S. Pat. No. 5,619,548 to Koppel and/or Published PCT Application No. WO 01/09566 to Rosencwaig, which are hereby incorporated by reference as if fully set forth herein, by eddy current measurements, by e-beam induced x-ray analysis, or by any other suitable method. Information related to processing of the reticle may be obtained from a fab database or a process tool as described herein, and the cause of the defect may be determined as described herein. Alternatively, such features may be extracted in step 130 and associated with the images manually classified by the user. In such an embodiment, the features of the manually classified images do not have to be extracted in step 136.

The method may also include automatic defect classification, as shown in step 138. Automatic defect classification may be performed using the features of the manually classified images extracted in step 136 and features of the remaining aerial images extracted in step 130 to automatically classify the remaining aerial images. For example, features of the remaining aerial images may be extracted and compared to the extracted features of the manually classified images. The extracted features that are selected for comparison may include all of the extracted features or a subset of the extracted features. The remaining images may be assigned a classification of the manually classified image or group of manually classified images that has the nearest extracted features. In addition, one or more of the extracted features may be weighted, and the manually classified image that has the nearest extracted features to a remaining image may be determined accordingly. The software described above may be operable to perform such automatic defect classification.

The method may optionally include comparing automatic defect classification results generated in step 138 to manual defect classification results generated in step 134, as shown in step 140. The results of such a comparison may be displayed to the user, as shown in step 142. The displayed results may also include results of the automatic defects classification. The user may use the results to alter the algorithm or another function used by the image computer for automatic classification or alter the manually classified images to alter the results of the automatic defect classification. Such an embodiment may also be implemented using any of the systems, interfaces, software, techniques, and additional steps of the methods as illustrated in PCT Publication No. WO 01/40145 to Baker et al., which is incorporated by reference as if fully set forth herein.

In an alternative embodiment, a method for classifying defects detected on a reticle may not include the manual classification steps as described above. In such an embodiment, therefore, the classification of defects may be substantially automatic. One embodiment of a method for substantially automatic classification of defects on a reticle is illustrated in the flow chart of FIG. 10. The method may include receiving input from an inspection system, as shown in step 144. The input may be image data representing an aerial image generated by an inspection or review subsystem as described above. The method may also include extracting features of defects in the aerial images, as described in step 146. The features may include any of the features as described above, and extracting the features may be performed using any of the techniques as described herein.

In addition, the method may include comparing the extracted features to features of classified defects in a database, as shown in step 148. The database may be a knowledge database that is generated and updated automatically. An example of a knowledge database that may be used for such a comparison is illustrated in U.S. Pat. No. 6,104,835 to Han, which is incorporated by reference as if fully set forth herein. The method may also include automatically classifying the defects in the aerial images based on the comparison, as shown in step 150. For example, automatic defect classification may include assigning a classification of the manually classified image or group of manually classified images having the nearest extracted features to a defect. The method may further include generating results of the automatic defect classification, as shown in step 152. The results may also be output to a number of modules such as a display medium, a printer, a storage medium, a database, and a fab database as described herein. For example, the image computer may be configured to access the fab database to send information to the fab database.

In an additional embodiment, step 148 may be replaced in the method described above using a different analytical routine. The analytical routine may include applying a number of filtering algorithms in series. Each filtering algorithm may identify only defects having a particular classification. The analytical routine may be performed using software that includes a plurality of cluster classification namespaces. The namespace may include a filename and an attribute, or a definition including a number of executable and other files. The files may include program instructions to retrieve procedures for the filtering algorithms included in an analytical routine and to execute the analytical routine. In a similar manner, the files may include program instructions such that the feature extraction and results display may also be applied in series before and after the analytical routine, respectively. Such software may provide flexibility in the types of defects that are classified in an analytical routine. For example, as defect classifications are developed, become obsolete, or are altered, the namespaces included the software may be altered to reflected such changes. Such an embodiment may also be implemented using any of the systems, interfaces, software, techniques, and additional steps of the methods as illustrated in U.S. Pat. No. 6,233,719 to Hardikar et al. and PCT Publication No. WO 99/22310 to Hardikar et al., which are incorporated by reference as if fully set forth herein.

Figure 9:
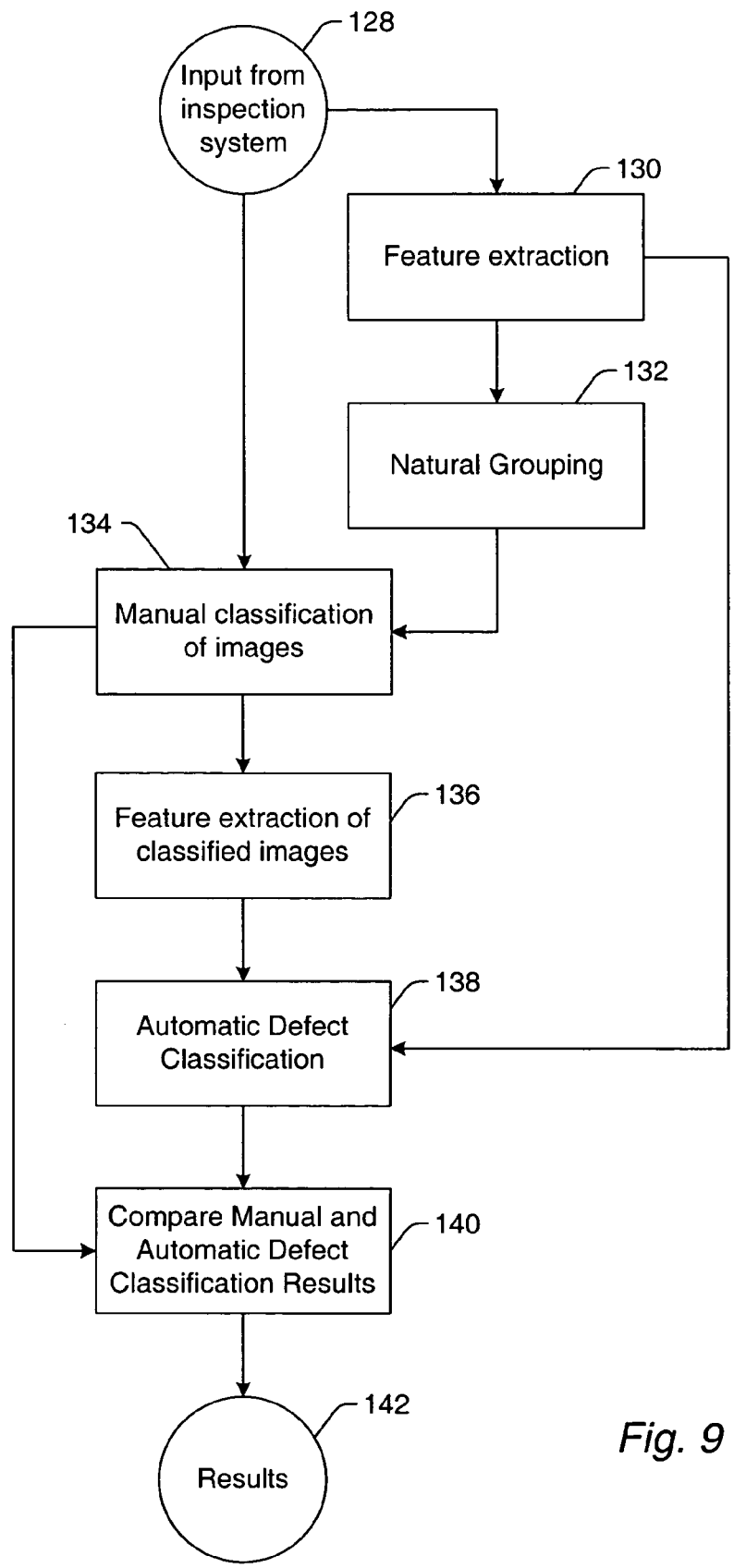

The results generated in the methods illustrated in FIGS. 9 and 10 may be displayed in a number of ways. For example, the results may be displayed such that defects having different classifications may be distinguished from each other. In such a display, defects having different classifications may be indicated by different colors, flags, or other designations. The results for one or more days may also be displayed in a bar chart or a two-dimensional map and the different classifications may be indicated by different colors, shading, background, flags, or any other such designation.

Image computer 126, as shown in FIG. 8, may be configured to perform additional functions such as detecting defects on the reticle using image data from the inspection subsystem and determining a root cause of the defects using image data from the inspection or review subsystem. Examples of root causes include, but are not limited to, chemical smears, grain, haze, microscoring, wand marks, brush marks, rail marks, impact marks, hot spots, shower patterns, exposure shutter patterns, doughnut patterns, poorly or unevenly developed layers on the reticle, over etching, under etching, and thermal variation. One embodiment of a method that the image computer may determine a root cause of defects on the reticle is illustrated in the flow chart of FIG. 11.

The method includes receiving input from an inspection system, as shown in step 154. The input may include image data generated by an inspection subsystem or a review subsystem as described herein. The method may also include feature extraction, as shown in step 156. Feature extraction may be performed as described herein. The features that are extracted in step 156 may include any of the features described above such as lateral dimension, shape, location, and proximity on the reticle to other features or defects. In addition, the method may include determining a root cause of the defects, as shown in step 158. The root cause of the defects may be determined using the image data received from the inspection subsystem or the review subsystem.

Figure 12:
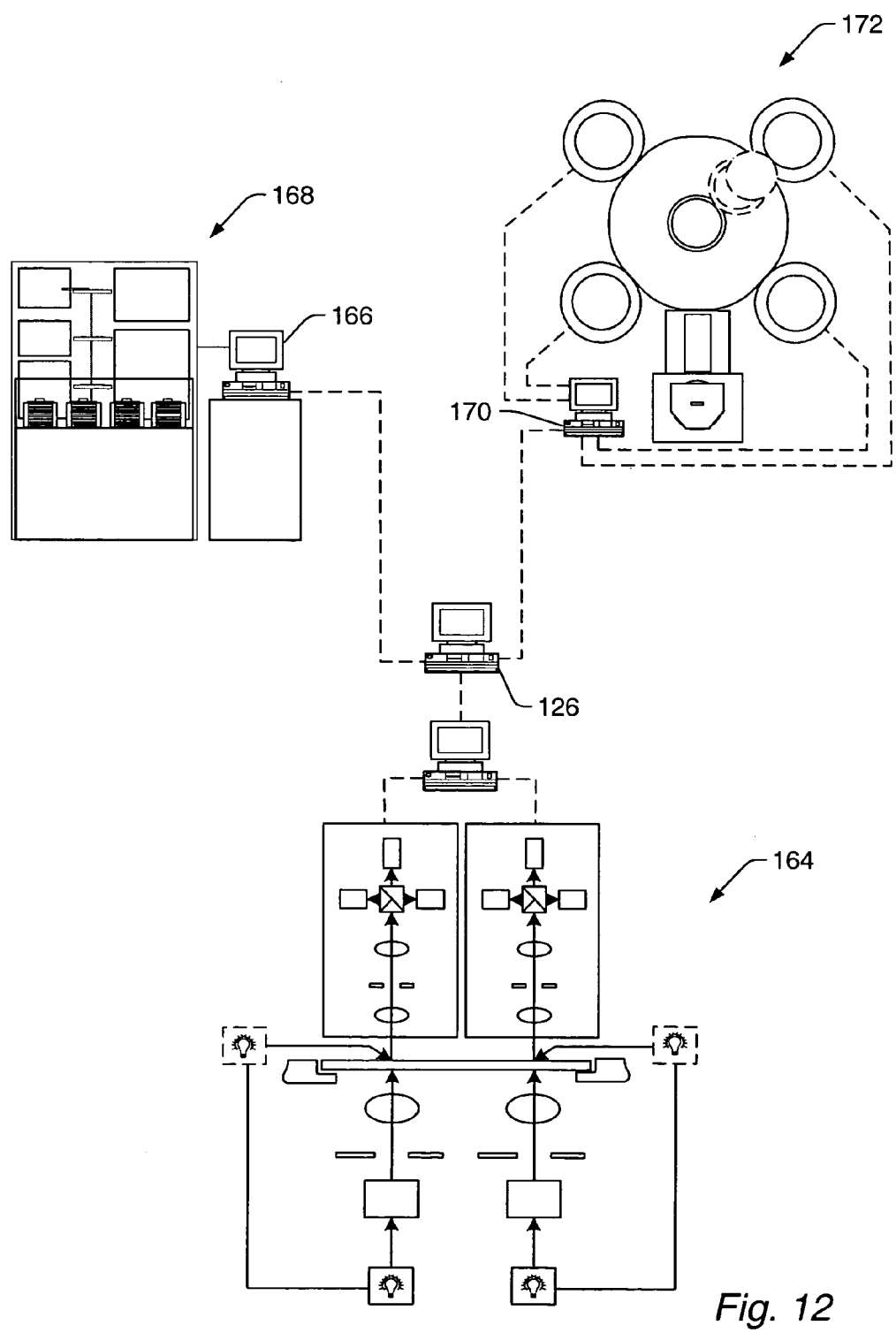
FIG. 12 depicts a schematic diagram of a side view of an inspection system that includes an image computer coupled to a lithography tool, shown in a side view, and an etch tool, shown in a top view.

In addition, the root cause of defects may also be determined taking into account other information related to parameters of processing of the reticle such as, but not limited to, time, temperature, tool, and tool history. Such information may be obtained from a fab database, which is described in more detail above, or from a processor coupled directly to a process tool. For example, the image computer may be configured to access a fab database and to retrieve information from the fab database related to processing of the reticle. Alternatively, the image computer may be coupled to one or more process tools, as shown in FIG. 12. Image computer 126 is shown in FIG. 12 coupled to inspection system 164, which is configured as illustrated in and described with respect to FIG. 6. The reference numerals of FIG. 6 are not included in FIG. 12 for simplicity. Image computer 126 may also be coupled to processor 166 of lithography tool 168 and processor 170 of etch tool 172. In this manner, the image computer may obtain information from lithography tool 168 and etch tool 172 related to processing of the reticle in these tools. One or more of the features extracted in step 156 may be used to determine a root cause of the defects.

Defects that have approximately the same features are likely to have the same cause. Determining a root cause of the defects may, therefore, include grouping the defects using various features of the defects described above to cluster defects that may have the same causation. In addition, defects that are located proximate to one another on a reticle or that occur in approximately the same location on more than one reticle may have the same causation. By analyzing properties of defects identified as belonging to the same cluster, a signature of the defects in that cluster may be determined and may be used to determine a root cause of the defects within the cluster. In addition, features of defects in a cluster may be determined based on the relationship of the defect to the other defects in the cluster.

Clustering as a technique for identifying groups of defects that may have the same causation is illustrated in U.S. Pat. No. 5,991,699 to Kulkarni et al., which is incorporated by reference as if fully set forth herein. The method described herein may further include any steps of the methods as described by Kulkarni et al. In addition, the method may include using software such as Klarity ACE root-cause analysis software available from KLA-Tencor to determine a root cause of the defects. The results of root cause determination may also be output to a number of modules such as a display medium, a printer, a storage medium, a database, and a fab database as described herein. For example, the image computer may be configured to access the fab database to send information related to the determined root causes of defects on the reticle to the fab database.

As shown in step 160, the method may also include determining corrective action that may be taken such that defects on the reticle or additional reticles may be reduced. Corrective action may include, for example, repairing the reticle to correct one or more defects on the reticle. Such repair may be performed as described above. The corrective action may also include determining other processing to be performed on the reticle such as additional cleaning or etching, which may be used to remove certain defects from the reticle. In addition, corrective action may include altering a parameter of a process that was used to fabricate the reticle. For example, the corrective action may include increasing the etch time of an etch process used to fabricate the reticle if a relatively large number of unwanted material defects were detected on the reticle. In this manner, additional reticles that may be processed using the etch process may have fewer defects than the reticle that was inspected. The corrective action may be determined using automated process control algorithms. An image computer as described herein may be configured to run such automated process control algorithms using the image data from the inspection subsystem or the review subsystem. Such automated process control algorithms may also be run using a software package such as Catalyst advanced process control (APC) commercially available from KLA-Tencor. Such process control algorithms generally describe a relationship between one or more parameters of a process or a process tool and a property of a reticle, a wafer, or an integrated circuit.

The method may also include implementing the corrective action, as shown in step 162. Implementing the corrective action may include providing the determined corrective action to a user. The user may manually implement the corrective action, for example, by altering a parameter of a process or a process tool. The parameter may be altered by manually changing the value of a parameter of a process or a process tool in a recipe configured to implement the process. For example, if the etch time of an etch process is to be increased as described above, the user may access a recipe that includes instructions related to steps of the etch process and values for various parameters of one or more steps of the etch process. The user may then increase the value for the etch time as indicated by the provided corrective action and store the altered recipe. In this manner, when the etch process is performed again, the user will select the recipe, which has been altered, and the etching will proceed for the lengthened period of time.

The corrective action may, alternatively, be implemented substantially automatically. For example, the image computer may be coupled to one or more process tools. As shown in FIG. 12, for example, image computer 126 may be coupled to processor 166 of lithography tool 168 and processor 170 of etch tool 172. The image computer may be configured to send information to the one or more process tools. For example, the image computer may send an identifier for a recipe for an etch process, an altered etch time, and an instruction to change the etch time in the recipe to the altered etch time to processor 170 of etch tool 172. In this manner, the image computer may alter a parameter of a process tool using a feedback control technique. In addition, the image computer may alter a parameter of a process tool using a feedforward control technique. For example, the image computer may be coupled to a processor of a repair tool. The image computer may send information to the processor of the repair tool indicating defects to be repaired on the reticle, characteristics of the defects such as location and size, classification, and even a recipe identifier and/or parameters of a repair process to be performed on the reticle.

The data described herein may be used not just to control process parameters, but also where desirable to control in situ endpointing and/or process control techniques. For example, data described herein may be used in conjunction with an apparatus such as that set forth in U.S. Pat. No. 5,689,614 to Gronet et al. and/or Published European Patent Application No. EP 1066925 A2 to Zuniga et al., which are hereby incorporated by reference as if fully set forth herein, to improve the control over localized heating of the reticle or closed loop control algorithms. Within reticle variation data could be fed forward or back to such a tool to optimize the algorithms used in control of local reticle heating, or even to optimize the tool design. In another example of such localized process control, within reticle variation data could be used to control or optimize a process or tool such as that set forth in one or more of Published PCT Patent Application Nos. WO 99/41434 to Wang or WO 99/25004 to Somekh et al. and/or Published European Patent Application No 1065567 A2 to Su, which are hereby incorporated by reference as if fully set forth herein.

Figure 13:
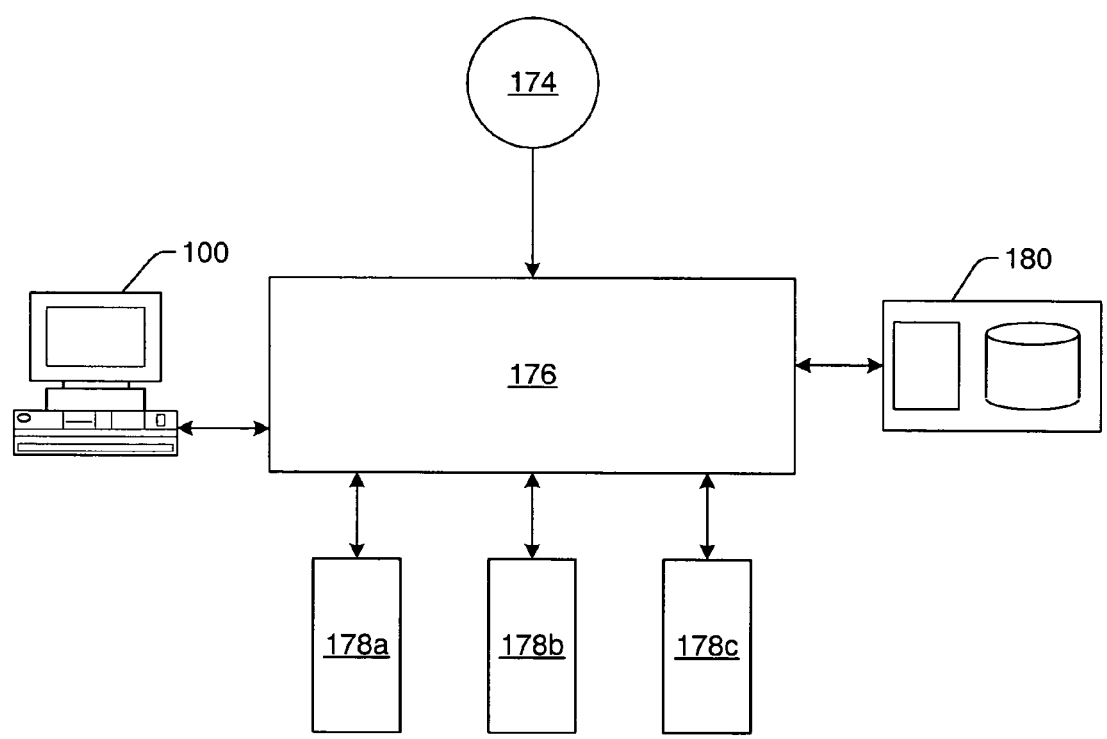
FIG. 13 illustrates a schematic diagram of an embodiment of a parallel processing system.

An image computer described herein may be configured as a parallel processing system. FIG. 13 illustrates a schematic diagram of an embodiment of a parallel processing system. The parallel processing system may be coupled to processor 100, which may be configured as described herein and illustrated in FIG. 6. The parallel processing system may be configured to receive image data representative of an aerial image of a reticle from an inspection system through processor 100. Alternatively, the parallel processing system may be coupled directly to the inspection system, and may be configured to receive image data 174 directly from the inspection system. The image data, in either example, may include one or more aerial images formed by light transmitted and/or reflected by the reticle. The parallel processing system may also include data distribution system 176, a number of processors 178a, 178b, 178c, and storage device 180. Although three processors 178a, 178b, and 178c are shown in FIG. 13, it is to be understood that such a system may include any number of such processors. In addition, the system may include a number of data distribution systems, which may be coupled in a "daisy chain" configuration. Each of the data distribution systems may be coupled to a plurality of processors as shown in FIG. 13. In this manner, the parallel processing system may be easily expanded, or otherwise altered, in response to the processing requirements of the overall inspection system and/or the requirements of a user of the system.

Data distribution system 176 may include buffers for temporarily storing the image data received from the inspection system. The data distribution system may be configured to send portions of the image data to processors 178a, 178b, and 178c. The image data sent to individual processors may include at least a portion of an aerial image of a reticle. For example, the memory of the data distribution system may be partitioned, and individual partitions may be coupled to one of the processors 178a, 178b, and 178c. In this manner, image data sent to a first partition may be sent to processor 178a, and image data sent to a second partition may be sent to processor 178b. If portions of an aerial image are sent to individual processors, the portions may correspond to, for example, a patch, a swath, or a die on the reticle. Image data representing an aerial image of the entire reticle may be divided into such portions using any method known in the art. For example, the portions may be determined based on coordinates associated with the image data representing a spatial position on the reticle. Instructions for how to divide the image data and information related to such division may be provided to the data distribution system by processor 100 or another processor of the parallel processing system. The size of the portions may also vary depending upon, for example, a memory size of processors 178a, 178b, and 178c.

Processors 178a, 178b, and 178c may include one or more microprocessors, interface and memory integrated circuits, and one or more shared and/or global memory devices. In addition, each processor 178a, 178b, and 178c may include a number of processors arranged on an appropriate semiconductor substrate such as a multi-chip module or a printed circuit board. Such processors may also include a shared memory device and a controller processor coupled to the individual processors.

Processors 178a, 178b, and 178c may also be configured to perform one or more functions on the image data received from the data distribution system. The one or more functions may include, for example, detecting defects on the reticle. The processors may be configured to detect defects on the reticle by comparing the image data to image data representative of a reference aerial image. The reference aerial image may be configured as described herein. The reference aerial image may be stored in storage device 180. The reference aerial image may be sent through data distribution system 176 to processors 178a, 178b, and 178c. In this manner, the data distribution system may also be configured to send appropriate portions of the image data representing the reference aerial image to the processors depending on how the image data from the inspection system was partitioned. Alternatively, the reference aerial image may be sent directly from storage device 180 to processors 178a, 178b, 178c through an appropriate interface and/or transmission medium.

The processors may also be configured to perform one or more functions on the reference aerial image prior to comparison to the image data received from the inspection system. For example, the processors may be configured to convert the image data representative of the reference aerial image into a form usable by the processors and altering the reference aerial image to simulate performance characteristics of the exposure system and the specimen as described above. Alternatively, the database may send data from a circuit pattern database to the processors, and the processors may generate the reference aerial image using the data in the circuit pattern database as described above.

The processors may also be configured to perform one or more functions subsequent to comparing the image data received from the inspection system. For example, the processors may be configured to send results of the defect detection to a display medium, a printer, a storage medium, a database, and a fab database as described herein, format the results to indicate features of the defects, classify the defects, determine a root cause of the defects, determine a designation of the region in which the defect was detected, and indicate the designation of the region in which the defect was detected.

The methods and/or algorithms that processors 178a, 178b, and 178c use to perform any of the one or more functions described above may vary depending on a number of variables such as, but not limited to, the reticle being inspected, the defects of interest, designations of one or more regions of the reference aerial image, and the inspection method performed on the reticle. Each of the processors may use the same method and/or algorithm to perform the one or more functions. Alternatively, each of the processors may use different algorithms or different parameters for the same algorithm depending on such variables. For example, if the image data sent to processor 178a is an aerial image of a portion of the reticle including critical regions and image data sent to processor 178b is an aerial image of a portion of the reticle including non-critical regions, processor 178a may use an algorithm having a more stringent detection threshold that processor 178b. The algorithm that each processor uses to perform the one or more functions may be determined by processor 100 or another processor of the parallel processing system and sent to processors 178a, 178b, and 178c through data distribution system.

Examples of a parallel processing system are illustrated and described in PCT Publication No. WO 00/68884 to Goldberg et al., which is incorporated by reference as if fully set forth herein. In addition, the image computer configured as a parallel processing system described above may also include additional components illustrated and described by Goldberg et al. Furthermore, the system and its individual components may be further configured as illustrated and described by Goldberg et al. An image computer, as described herein, provides a system for efficient processing of image data. In addition, such an image computer reduces setbacks due to failure of processors because the parallel processing system include a number of processors. Therefore, the image computer can continue to process image data in spite of a failed processor.

An image computer, or another processor described herein, may be configured to analyze the detected defects to determine if too many or too few defects are being detected or if one or more types of defects are undesirably being detected or not being detected. Detection of too many or too few defects indicates that the sensitivity of an inspection system or an inspection subsystem is not appropriately set for the desired accuracy. Therefore, the image computer, or a processor, may alter a sensitivity of the inspection system or subsystem. For example, the image computer, or a processor, may alter a threshold or an algorithm being used to detect defects on a reticle. In addition, a processor may also be configured to control one or more components of an inspection system or subsystem to alter a parameter of the components. For example, a processor may alter a parameter of an illumination subsystem or a collection subsystem such that a different number of defects may be detected by the system.

The printability of defects changes as the wavelength of illumination changes. Therefore, in the past, aerial inspection of reticles was often performed at the wavelength of the exposure system to determine the effect of the defect on images printed by the exposure system. In this manner, as the wavelength of light used in exposure systems is decreased to improve resolution of these systems, wavelength of illumination in inspection systems must also be decreased proportionally. Decreasing the wavelength of illumination of the inspection systems, however, increases the cost and complexity of such systems. For example, as the wavelength decreases, the optical components of the inspection system may have to be redesigned to avoid problems associated with interactions between materials of the optical components and the light. In addition, the illumination wavelength of the inspection systems must be stringently controlled to match the control requirements of exposure systems. For example, the illumination system must be controlled to avoid drift in the wavelength of the illumination thereby reducing the accuracy of detection of defects that will print at the wavelength of the exposure system. Furthermore, such inspection systems do not properly account for variations that may exist between the exposure system and the inspection system or between different exposure systems. Therefore, inspection at a wavelength of the exposure system may not accurately reflect printability of defects at the wavelength of the exposure system. In this manner, defects that will be printed by an exposure system may not be detected using such an inspection system due to such variations.

In an embodiment, a method for inspecting a reticle may include forming an aerial image of the reticle with an inspection system at a wavelength different from a wavelength of an exposure system. The inspection system may include any of the inspection systems as described herein. For example, the inspection system may be configured as illustrated and described with respect to FIGS. 1–2, 6–8, and 12. The exposure system may be configured to print an image of a reticle onto a specimen at a wavelength of, for example, 248 nm, 193 nm, or 157 nm. The inspection system, however, may be configured to form an aerial image of the reticle at a wavelength of, for example, about 196 nm or about 248 nm. In addition, the inspection system may be configured to form an aerial image of the reticle at a wavelength of about 193 nm, but the wavelength of such a system may not need stringent controls to maintain the wavelength at 193 nm. Instead, the wavelength may be monitored over time and recorded such that the wavelength of light that was used to form an aerial image of a reticle may be obtained.

It may be possible to use any wavelength of light to form an aerial image of a reticle, however, imaging capability generally degrades as the wavelength of light increases if other parameters are constant. Appropriate wavelengths of light for the inspection system may include any wavelength of light short enough such that the inspection system may form an aerial image of the reticle that is at least partially resolved. For example, the wavelength of illumination of the inspection system may be sufficiently short such that contrast of an aerial image of the reticle is greater than 0. In other words, the aerial image may only be resolved such that features and other characteristics of the aerial image are discernable to an algorithm or image processing software. Therefore, such an aerial image may have significantly poorer resolution and other image qualities such as contrast than an image of the reticle that would be printed by an exposure system. Such appropriate wavelengths may be less than about 400 nm but may also vary depending upon, for example, dimensions of features on the reticle, spatial frequency of features on the reticle, a partial coherence of the inspection system, a numerical aperture of the inspection system, and the type of illumination used (i.e., off-axis, quadrapole, etc.).

Imaging capability of an optical system such as an inspection system and an exposure system depends on several parameters including wavelength of illumination, reticle feature size, numerical aperture of the lens, and spatial coherence of the illumination. When an image is formed by an optical system, the resulting image will be somewhat degraded due to aberrations and diffraction phenomena, in addition to minute assembly and alignment errors in the optics. In this image, bright highlights may not appear as bright as they do in the reticle, and dark or shadowed areas will not be as black as those observed in the original patterns.

Image contrast, or modulation, is defined as: Modulation $(M)=(I_{max}-I_{min})/(I_{max}+I_{min})$ where $I_{max}$ is the maximum intensity displayed by a repeating structure in a specimen and $I_{min}$ is the minimum intensity found in the same specimen. Modulation indicates the degree to which diffraction effects cause incident radiation to fall between images of two features of a reticle. Modulation can be determined at the object (reticle) plane and at the image (specimen) plane. Modulation transfer function (MTF) of an optical system can be expressed at the ratio of the modulation in the image plane to that in the object plane, $M_{im}/M_{object}$. In this manner, MTF is a measurement of the ability of the optical system to transfer contrast from a reticle to an intermediate image plane at a specific resolution. Therefore, MTF provides an indication of the performance characteristics of an optical system such as an inspection system to form an aerial image of a reticle as described herein or an exposure system to print an image of a reticle on a specimen.

The reticle may include a pattern of a periodic grid (lines and spaces) with substantially equal linewidths. The number of spacings per unit interval in a reticle may be referred to as the spatial frequency, which is usually expressed in quantitative terms of the periodic spacings (spatial period) found in the reticle. Modulation of the output signal, or the intensity of light waves forming an image of the reticle, corresponds to the formation of image contrast. Therefore, a measure of the MTF for an optical system may be obtained from the contrast generated by periodic lines or spacings present in a reticle that result from sinusoidal intensities in the image that vary as a function of spatial frequency. By convention, the modulation transfer function is normalized to unity at zero spatial frequency.

When there are no significant aberrations present in an optical system, the modulation transfer function is related to the size of the diffraction pattern, which is a function of the system numerical aperture and wavelength of illumination. Therefore, because the inspection system and the exposure system have different wavelengths of illumination, these systems will have different modulation transfer functions. It is noted that the inspection system and the exposure systems may or may not have different numerical apertures because such differences may also be accounted for by correcting an aerial image for differences in the modulation transfer functions as described herein. In quantitative terms, the modulation transfer function for an optical system with a substantially uniformly illuminated circular aperture may be expressed as:

$$MTF = 2(\phi - \cos\phi \sin\phi)/\pi, \text{ where}$$

$$\phi = \cos^{-1}(\lambda v / 2NA)$$

and where $v$ is the spatial frequency in spacings per millimeter, $\lambda$ is the wavelength of illumination, and NA is the numerical aperture. Therefore, if the spatial frequency of the reticle, the wavelength of illumination and the numerical aperture of the optical system are known, the MTF may be calculated. At low spatial frequencies, image contrast is highest, but falls to zero as the spatial frequency is increased beyond a certain point. The cutoff, ($f(c)$), is the spatial frequency at which contrast reaches zero and can be expressed by the equation:

$$f(c) = 2NA/\lambda.$$

This equation illustrates that resolution increases with numerical aperture and reduced wavelength.

Alternatively, the MTF of an optical system may be estimated by imaging a reticle that includes a test pattern onto a specimen. The test pattern may include high-contrast periodic line gratings having a series of spacings that have a range of lateral dimensions. Such a measurement also depends upon modulation of the specimen. The modulation transfer function is wavelength dependent. Therefore, such measurement should be performed under carefully defined conditions of illumination. Such measurements may also be made at various focus settings and at various levels of other parameters of the optical system. As the specimen plane moves out of focus, contrast drops rapidly for features having high spatial frequencies and more slowly for features having low spatial frequencies. Therefore, contrast may be measured at a particular spatial frequency and as a function of distance from the image plane. Such analysis may be referred to as a through-focus transfer function and is a measure of depth of focus for an optical system. The modulation transfer functions of individual components of an optical system may be multiplied to obtain an overall MTF for an optical system. The MTF of the inspection system and the exposure system may be determined using one of the methods described above. In addition, the MTF of exposure systems may be available from the manufacturers of commercially available exposure systems.

Such a method also includes correcting the aerial image for differences between modulation transfer function of the inspection system and the exposure system. Any of the processors, or an image computer, as described herein may be configured to correct the aerial image in this manner. Correcting the aerial image may include altering the aerial image to simulate performance characteristics of the exposure system and the specimen. For example, a simulation program such as PROLITH as described above may be combined with other software such as the Klarity ProDATA AutoTune module described above to simulate performance characteristics of the exposure system and the specimen. Therefore, aerial images that would be formed by the inspection system at the wavelength of illumination of the exposure system may be determined from a single aerial image of the reticle formed by an inspection system at a different wavelength. In this manner, the corrected aerial image may be substantially equivalent to an image of the reticle that would be printed onto a specimen by the exposure system at the wavelength of the exposure system.

The method may also include detecting defects on the reticle using the corrected aerial image. Any of the processors, or an image computer, as described herein may be configured to detect defects on the reticle using the corrected aerial image. Detecting defects may be performed using any of the methods as described herein. For example, defects on the reticle may be detected by comparing the aerial image of the reticle formed by the inspection system to a reference image of the reticle, which may be commonly referred to as a die:database comparison. The reference image may be substantially equivalent to an image of the reticle that would be printed by the exposure system. Alternatively, defects on the reticle may be detected by comparing one portion of the aerial image of the reticle to another portion of the aerial image, which may be commonly referred to as a die:die comparison. In addition, an aerial image of the reticle formed by light transmitted by the reticle may be compared to an aerial image of the reticle formed by light reflected by the reticle. The method may also include performing one or more other functions on image data representing the corrected aerial image as described above.

As described above, the aerial image formed by the inspection system is corrected for differences between modulation transfer functions of the inspection system and the exposure system. Therefore, comparing the aerial image to a reference image that is substantially equivalent to an image of the reticle that would be printed by an exposure system will reduce, or even eliminate, the detection of nuisance defects. In this manner, a substantial portion of the defects may include defects that would be printed onto the specimen by the exposure system using the reticle. In addition, the detected defects may include substantially all of the defects that would be printed onto a specimen by the exposure system using the reticle. As such, the method may detect printable defects on a reticle more accurately than currently available methods for aerial inspection of reticles.

In an embodiment, the method may also include altering a parameter of the inspection system in response to variations in a parameter of the exposure system. For example, the partial coherence of the inspection system may be altered in response to a change in the partial coherence of the exposure system. The parameter may be altered by a processor coupled to the system. For example, the processor may be coupled to an adjustable aperture and may be configured to alter a numerical aperture of the adjustable aperture to alter the partial coherence of the system. Other parameters of the inspection system that may be altered include, for example, focus settings of the detectors as described above.

Alternatively, the method may include altering the corrected aerial image to determine an image of the reticle that would be printed onto the specimen by the exposure system at various levels of a parameter of the exposure system. For example, the corrected aerial image may be altered to determine an image of the reticle that would be printed onto the specimen by the exposure system at various focus settings and/or various exposure dose settings. The corrected aerial image may be altered using a simulation program as described herein. In addition, any of the processors, or an image computer, as described herein may be configured to alter the corrected aerial image.

In an embodiment, the methods described herein may include altering the corrected aerial image to determine variations across the image that would be printed by the exposure system due to variations of a parameter of the exposure system across the reticle. Variations of a parameter of an exposure system across a reticle may be caused by a number of different components included in the exposure system. For example, aberrations across a lens may produce variations in illumination across the reticle. Aberrations in a lens may include variations in shape and thickness of the material used to form the lens, inhomogeneous lens materials, improper lens mounting, spacing or tilting of the lens, or other imperfections in the lens caused by manufacturing. Properties of a lens may also change over time due to, for example, incorrect wavelength of illumination, tilting of a reticle or a specimen, and incorrect environmental conditions.

The method may include determining variations of a parameter of the exposure system across the reticle. For example, aberrations across a lens may be determined using lens design software. In addition, such aberrations may be measured using an optical technique such as interferometry. Such measurements may be used to determine characteristics of the lens as a function of position by fitting the data to a polynomial such as the Zernike polynomial, which is known in the art, for various positions across the field of the lens. Coefficients of such a polynomial determined for the fitted data may provide insight into the characteristics of the lens. Therefore, the determined or measured aberrations as a function of spatial position across the lens may be used to determine variations in a parameter such as phase of illumination of the exposure system as a function of spatial position across the lens and in turn across the reticle.

Other parameters of the exposure system that may vary across the reticle may also be determined and/or monitored over time using a device that is sensitive to the parameter as a function of spatial position. Such a device may be coupled to the component of the exposure system, which causes the variation, or arranged within the exposure system at a position at which the parameter may be measured.

Such variations of the exposure system across the reticle will affect an image printed by different reticles in different ways. For example, different reticles features will diffract light differently thereby directing light to different positions on the lens. Therefore, characteristics of the lens produce different effects on the printed images of different reticles depending upon reticle feature type, size, and orientation. The corrected aerial image may be altered to account for such variations across the reticle using a simulation program and a processor or image computer as described herein and incorporating data representing such variations into the simulation program. In this manner, by altering the corrected aerial image to account for such variations across the reticle, the defects that are detected may reflect defects that will be printed by the exposure system more accurately than currently available aerial inspection methods and systems.

The method may also include altering the corrected aerial image to determine images of the reticle that would be printed onto the specimen by a plurality of exposure systems of the same make and model of the exposure system. Although exposure systems of the same make and model may have the same design, the systems may have different parameters due to variations in arrangement and configuration of the optical components between the systems. For example, the lenses of the systems may have different optical properties and may have different optical properties across the lenses as described above. Therefore, exposure systems of the same make and model may have difference imaging capabilities. The corrected aerial image may be altered to account for such variations between exposure systems using a simulation program and a processor or image computer as described herein and incorporating data representing such variations into the simulation program.

In this manner, the method may also be used to compare the performance of several exposure systems. In addition, the method may be used to select which exposure systems are used to print images of a particular reticle onto a specimen. For example, the printability of defects on reticle for a number of exposure systems may be compared, and the exposure system that prints the fewest number of defects on the specimen or that has the largest process window, which may be determined as described herein, may be selected to use the reticle. Such a comparison may also be used, for example, in a manufacturing environment in which several exposures systems may be used in parallel to manufacture integrated circuits or other semiconductor devices. Such exposure systems used in parallel in a common fabrication facility may be of the same make and model. A fabrication facility, however, typically includes a plurality of steppers of different makes and models. The method may also be used to determine images of the reticle that would be printed onto a specimen by different makes and models of exposure systems as described above. In this manner, the method may be used to characterize all of the exposure systems in a fabrication facility.

In an alternative embodiment, a method for inspecting a reticle may include forming an aerial image of the reticle with an inspection system at a wavelength different from a wavelength of an exposure system. The inspection system may have a modulation transfer function approximately equal to a modulation transfer function of the exposure system. For example, as described above, the modulation transfer function depends upon at least wavelength of illumination and numerical aperture. In addition, the modulation transfer function of an exposure system may be determined using one of the methods described above. In this manner, if the wavelength of illumination of the inspection system is known, the numerical aperture of the inspection system may be selected such the inspection system has a modulation transfer function substantially equal to a modulation transfer function of the exposure system. Therefore, an aerial image of the reticle formed by the inspection system may be substantially equivalent to an image of the reticle that would be printed by the exposure system although the inspection system and the exposure system have different wavelengths of illumination. As such, correcting the aerial image for differences between the modulation transfer functions of the inspection and exposure systems described above may not be included in this method.

The method may also include any of the steps described in other embodiments of methods described herein. For example, the method may include altering a parameter of the inspection system in response to variations in a parameter of the exposure system as described above. Therefore, the inspection system may have substantially the same parameters and modulation transfer function of the exposure system, and an aerial image of such an inspection system may not be corrected prior to defect detection. Such a method may also include detecting defects on the reticle using the aerial image as described above. The method may also include altering the aerial image as described above.

Additional examples of methods and systems for detecting defects on a surface of a reticle or another specimen are illustrated in U.S. Pat. No. 4,247,203 to Levy et al., U.S. Pat. No. 4,347,001 to Levy et al., U.S. Pat. No. 4,378,159 to Galbraith, U.S. Pat. No. 4,448,532 to Joseph et al., U.S. Pat. No. 4,532,650 to Wihl et al., U.S. Pat. No. 4,555,798 to Broadbent, Jr. et al., U.S. Pat. No. 4,579,455 to Levy et al., 4,633,504 to Wihl, U.S. Pat. No. 4,641,967 to Pecen, U.S. Pat. No. 4,758,094 to Wihl et al., U.S. Pat. No. 4,766,324 to Saadat et al., U.S. Pat. No. 4,805,123 to Specht et al., U.S. Pat. No. 4,845,558 to Tsai et al., U.S. Pat. No. 4,877,326 to Chadwick et al., U.S. Pat. No. 4,926,489 to Danielson et al., U.S. Pat. No. 5,189,481 to Jann et al., U.S. Pat. No. 5,563,702 to Emery et al., U.S. Pat. No. 5,572,598 to Wihl et al., U.S. Pat. No. 5,737,072 to Emery et al., U.S. Pat. No. 5,889,593 to Bareket, U.S. Pat. No. 6,052,478 to Wihl et al., U.S. Pat. No. 6,076,465 to Vacca et al., U.S. Pat. No. 6,122,046 to Almogy, U.S. Pat. No. 6,137,570 to Chuang et al., U.S. Pat. No. 6,141,038 to Young et al., U.S. Pat. No. 6,175,645 to Elyasaf et al., U.S. Pat. No. 6,282,309 to Emery, and U.S. Pat. No. 6,363,166 to Wihl et al. to all of which are incorporated by reference as if fully set forth herein. Additional examples of defect inspection methods and apparatuses are illustrated in PCT Application Nos. WO 99/38002 to Elyasaf et al. and WO 00/70332 to Lehan, which are incorporated by reference as if fully set forth herein. Further examples of defect inspection methods and apparatuses are illustrated in European Patent Application Nos. EP 1 061 358 A2 to Dotan, EP 1 061 571 A2 to Ben-Porath, and EP 1 069 609 A2 to Harvey et al., which are incorporated by reference as if fully set forth herein. As such, the embodiments described above may also include features of any of the systems and methods illustrated in all of the patents which have been incorporated by reference herein.

Further modifications and alternative embodiments of various aspects of the invention may be apparent to those skilled in the art in view of this description. For example, methods and systems for inspecting a reticle are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for inspecting a reticle, comprising:
    forming an aerial image of the reticle with an inspection system at a wavelength different from a wavelength of an exposure system;
    correcting the aerial image for differences between modulation transfer functions of the inspection system and the exposure system such that the corrected aerial image is substantially equivalent to an image of the reticle that would be printed onto a specimen by the exposure system at the wavelength of the exposure system; and
    detecting defects on the reticle using the corrected aerial image.

2. The method of claim 1, further comprising altering a parameter of the inspection system in response to variations in a parameter of the exposure system.

3. The method of claim 1, further comprising altering the corrected aerial image to determine images of the reticle that would be printed onto the specimen by the exposure system at various levels of a parameter of the exposure system.

4. The method of claim 1, further comprising altering the corrected aerial image to determine images of the reticle that would be printed onto the specimen by the exposure system at various focus settings of the exposure system.

5. The method of claim 1, further comprising altering the corrected aerial image to determine images of the reticle that would be printed onto the specimen by the exposure system at various dose settings of the exposure system.

6. The method of claim 1, further comprising altering the corrected aerial image to determine variations across the image that would be printed onto the specimen by the exposure system due to variations of a parameter of the exposure system across the reticle.

7. The method of claim 1, further comprising altering the corrected aerial image to determine images of the reticle that would be printed onto the specimen by a plurality of exposure systems of the same make and model as the exposure system.

8. The method of claim 1, further comprising altering the corrected aerial image to determine images of the reticle that would be printed onto the specimen by a plurality of exposure systems used in a common fabrication facility.

9. The method of claim 1, wherein a substantial portion of the defects comprises defects that would be printed onto the specimen by the exposure system using the reticle.

10. A method for inspecting a reticle, comprising:
    forming an aerial image of the reticle with an inspection system at a wavelength different from a wavelength of an exposure system, wherein the inspection system has a modulation transfer function approximately equal to a modulation transfer function of the exposure system; and
    detecting defects on the reticle using the aerial image.

11. The method of claim 10, further comprising altering a parameter of the inspection system in response to variations in a parameter of the exposure system.

12. A system configured to inspect a reticle, comprising:
    an inspection system configured to form an aerial image of the reticle at a wavelength different from a wavelength of an exposure system; and
    a processor configured to correct the aerial image for differences between modulation transfer functions of the inspection system and the exposure system such that the corrected aerial image is substantially equivalent to an image of the reticle that would be printed onto a specimen by the exposure system at the wavelength of the exposure system and to detect defects on the reticle using the corrected aerial image.

13. The system of claim 12, wherein the processor is further configured to alter a parameter of the inspection system in response to variations in a parameter of the exposure system.

14. The system of claim 12, wherein the processor is further configured to alter the corrected aerial image to determine images of the reticle that would be printed onto the specimen by the exposure system at various levels of a parameter of the exposure system.

15. The system of claim 12, wherein the processor is further configured to alter the corrected aerial image to determine images of the reticle that would be printed onto the specimen by the exposure system at various focus settings of the exposure system.

16. The system of claim 12, wherein the processor is further configured to alter the corrected aerial image to determine images of the reticle that would be printed onto the specimen by the exposure system at various dose settings of the exposure system.

17. The system of claim 12, wherein the processor is further configured to alter the corrected aerial image to determine variations across the image that would be printed onto the specimen by the exposure system due to variations of a parameter of the exposure system across the reticle.

18. The system of claim 12, wherein the processor is further configured to alter the corrected aerial image to determine images of the reticle that would be printed onto the specimen by a plurality of exposure systems of the same make and model as the exposure system.

19. The system of claim 12, wherein the processor is further configured to alter the corrected aerial image to determine images of the reticle that would be printed onto the specimen by a plurality of exposure systems used in a common fabrication facility.

20. The system of claim 12, wherein a substantial portion of the defects comprises defects that would be printed onto the specimen by the exposure system using the reticle.

* * * * *